US012692298B2

(12) United States Patent
Gao et al.

(10) Patent No.: US 12,692,298 B2
(45) Date of Patent: Jul. 28, 2026

(54) SCREENING AND ANTITUMOR USE OF KRAS MUTATION SPECIFIC T CELL RECEPTOR

(71) Applicant: Institute of Microbiology, Chinese Academy of Sciences, Beijing (CN)

(72) Inventors: Fu Gao, Beijing (CN); Shuguang Tan, Beijing (CN); Dan Lu, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 702 days.

(21) Appl. No.: 18/247,018

(22) PCT Filed: Sep. 29, 2021

(86) PCT No.: PCT/CN2021/121576
§ 371 (c)(1),
(2) Date: Mar. 28, 2023

(87) PCT Pub. No.: WO2022/068850
PCT Pub. Date: Apr. 7, 2022

(65) Prior Publication Data
US 2023/0374101 A1     Nov. 23, 2023

(30) Foreign Application Priority Data
Sep. 29, 2020    (CN) .......................... 202011047695.0

(51) Int. Cl.
| | |
|---|---|
| *C07K 14/725* | (2006.01) |
| *A61P 35/00* | (2006.01) |
| *C07K 14/705* | (2006.01) |
| *G01N 33/575* | (2026.01) |

(52) U.S. Cl.
CPC .......... *C07K 14/7051* (2013.01); *A61P 35/00* (2018.01); *G01N 33/5758* (2026.01); *G01N 2333/7051* (2013.01)

(58) Field of Classification Search
CPC ............................. C07K 14/7051; A61P 35/00
See application file for complete search history.

(56) References Cited

U.S. PATENT DOCUMENTS

2017/0319638 A1    11/2017  Conner et al.
2019/0177395 A1*    6/2019  Tran ................... C07K 14/7051

FOREIGN PATENT DOCUMENTS

| CN | 108137685 A | 6/2018 |
|---|---|---|
| CN | 112300269 A | 2/2021 |
| WO | 2016/154246 A1 | 9/2016 |
| WO | 2020041501 A1 | 2/2020 |

OTHER PUBLICATIONS

Office Action issued in CA 3,193,963, dated Jun. 11, 2025.
Office Action issued in JP 2023-519189, dated Jun. 19, 2025.
Office Action issued in KR 10-2023-7014640, dated Jul. 14, 2025.
Lu, D., et al., "KRAS G12V neoantigen specific T cell receptor for adoptive T cell therapy against tumors," *Nat. Commun.* 14:6389 pp. 1-16 (2023).
Extended European Search Report for European Application No. 21874505.7 mailed Nov. 13, 2024.
International Search Report of PCT/CN2021/121576, Jan. 4, 2022.
Qin et al., A method of screening highly common neoantigens with immunogenicity in colorectal cancer based on public somatic mutation library, Hereditas, 2020, 42(6):599-612. (pp. 602, 607). With English Abstract.
Wang et al., Identification of T-cell receptors targeting KRAS-mutated humantumors, Cancer Immunol Res., 2016, 4(3):204-214.
Examination Report of Canadian Patent Application No. 3,193,963, mailed Apr. 17, 2024.

* cited by examiner

*Primary Examiner* — Aurora M Fontainhas
*Assistant Examiner* — Jennifer A Benavides
(74) *Attorney, Agent, or Firm* — Medler Ferro Woodhouse & Mills PLLC

(57)          ABSTRACT

The present disclosure provides two specific T cell receptors targeting a G12V or G12C mutant epitope of a KRAS gene, and an anti-tumor use thereof. Each of the two T cell receptors consists of an α peptide chain and a β peptide chain. Further provided are an antigen binding fragment of the T cell receptors, a nucleic acid encoding the T cell receptors or an antigen binding fragment thereof, a vector comprising the nucleic acid, and a host cell comprising the vector. Further provided is a method for preparing a specific T cell receptor for a KRAS G12V mutation or an antigen-binding fragment thereof. The specific T cell receptor and antigen-binding fragment thereof can be used as an immune activator to stimulate an immune response of an organism, thereby generating an effect against tumors and other diseases.

15 Claims, 7 Drawing Sheets

Specification includes a Sequence Listing.

SEQUENCE LISTING

<160> NUMBER OF SEQ ID NOS: 48

<210> SEQ ID NO 1
<211> LENGTH: 333
<212> TYPE: DNA
<213> ORGANISM: Artificial
<220> FEATURE:
<223> OTHER INFORMATION: Artificially synthesized sequence

<400> SEQUENCE: 1

```
caacagaagg tgcagcagag cccagaatcc ctcattgttc cagagggagg catggcctct        60
ctcaactgca cttccagtga tcgtaatgtt gactacttct ggtggtacag acagcactct       120
gggaaaagcc ccaagatgct gatgtctatc ttctccaatg gtgaaaagga agaaggcaga       180
ttcacagttc acctcaataa agccagcctg catacttccc tgcacatcag agactcccag       240
cccagtgact ctgctctcta cctctgtgca gcaagggaca gcaactatca gttgatctgg       300
ggctctggga ccaagctaat tataaagcca gat                                     333
```

<210> SEQ ID NO 2
<211> LENGTH: 111
<212> TYPE: PRT
<213> ORGANISM: Artificial
<220> FEATURE:

-continued

<223> OTHER INFORMATION: Artificially synthesized sequence

<400> SEQUENCE: 2

Gln Gln Lys Val Gln Gln Ser Pro Glu Ser Leu Ile Val Pro Glu Gly
1               5                   10                  15

Gly Met Ala Ser Leu Asn Cys Thr Ser Ser Asp Arg Asn Val Asp Tyr
            20                  25                  30

Phe Trp Trp Tyr Arg Gln His Ser Gly Lys Ser Pro Lys Met Leu Met
        35                  40                  45

Ser Ile Phe Ser Asn Gly Glu Lys Glu Glu Gly Arg Phe Thr Val His
    50                  55                  60

Leu Asn Lys Ala Ser Leu His Thr Ser Leu His Ile Arg Asp Ser Gln
65                  70                  75                  80

Pro Ser Asp Ser Ala Leu Tyr Leu Cys Ala Ala Arg Asp Ser Asn Tyr
                85                  90                  95

Gln Leu Ile Trp Gly Ser Gly Thr Lys Leu Ile Ile Lys Pro Asp
            100                 105                 110

<210> SEQ ID NO 3
<211> LENGTH: 6
<212> TYPE: PRT
<213> ORGANISM: Artificial
<220> FEATURE:
<223> OTHER INFORMATION: Artificially synthesized sequence

<400> SEQUENCE: 3

Asp Arg Asn Val Asp Tyr
1               5

<210> SEQ ID NO 4
<211> LENGTH: 6
<212> TYPE: PRT
<213> ORGANISM: Artificial
<220> FEATURE:
<223> OTHER INFORMATION: Artificially synthesized sequence

<400> SEQUENCE: 4

Ile Phe Ser Asn Gly Glu
1               5

<210> SEQ ID NO 5
<211> LENGTH: 10
<212> TYPE: PRT
<213> ORGANISM: Artificial
<220> FEATURE:
<223> OTHER INFORMATION: Artificially synthesized sequence

<400> SEQUENCE: 5

Ala Ala Arg Asp Ser Asn Tyr Gln Leu Ile
1               5                   10

<210> SEQ ID NO 6
<211> LENGTH: 336
<212> TYPE: DNA
<213> ORGANISM: Artificial
<220> FEATURE:
<223> OTHER INFORMATION: Artificially synthesized sequence

<400> SEQUENCE: 6
gaggctgcag tcacccaaag cccaagaaac aaggtggcag taacaggagg aaaggtgaca      60
ttgagctgta atcagactaa taaccacaac aacatgtact ggtatcggca ggacacgggg     120
catgggctga ggctgatcca ttattcatat ggtgctggca gcactgagaa aggagatatc     180

-continued cctgatggat acaaggcctc cagaccaagc caagagaact tctccctcat tctggagttg     240 gctacccct  ctcagacatc agtgtacttc tgtgccagcg gtgatacagg gggctatgaa     300
cagtacttcg gtcccggcac caggctcacg gtttta                              336

<210> SEQ ID NO 7
<211> LENGTH: 112
<212> TYPE: PRT
<213> ORGANISM: Artificial
<220> FEATURE:
<223> OTHER INFORMATION: Artificially synthesized sequence

<400> SEQUENCE: 7

Glu Ala Ala Val Thr Gln Ser Pro Arg Asn Lys Val Ala Val Thr Gly
1               5                   10                  15

Gly Lys Val Thr Leu Ser Cys Asn Gln Thr Asn Asn His Asn Asn Met
            20                  25                  30

Tyr Trp Tyr Arg Gln Asp Thr Gly His Gly Leu Arg Leu Ile His Tyr
        35                  40                  45

Ser Tyr Gly Ala Gly Ser Thr Glu Lys Gly Asp Ile Pro Asp Gly Tyr
    50                  55                  60

Lys Ala Ser Arg Pro Ser Gln Glu Asn Phe Ser Leu Ile Leu Glu Leu
65                  70                  75                  80

Ala Thr Pro Ser Gln Thr Ser Val Tyr Phe Cys Ala Ser Gly Asp Thr
                85                  90                  95

Gly Gly Tyr Glu Gln Tyr Phe Gly Pro Gly Thr Arg Leu Thr Val Leu
            100                 105                 110

<210> SEQ ID NO 8
<211> LENGTH: 5
<212> TYPE: PRT
<213> ORGANISM: Artificial
<220> FEATURE:
<223> OTHER INFORMATION: Artificially synthesized sequence

<400> SEQUENCE: 8

Asn Asn His Asn Asn
1               5

<210> SEQ ID NO 9
<211> LENGTH: 6
<212> TYPE: PRT
<213> ORGANISM: Artificial
<220> FEATURE:
<223> OTHER INFORMATION: Artificially synthesized sequence

<400> SEQUENCE: 9

Ser Tyr Gly Ala Gly Ser
1               5

<210> SEQ ID NO 10
<211> LENGTH: 11
<212> TYPE: PRT
<213> ORGANISM: Artificial
<220> FEATURE:
<223> OTHER INFORMATION: Artificially synthesized sequence

<400> SEQUENCE: 10

Ala Ser Gly Asp Thr Gly Gly Tyr Glu Gln Tyr
1               5                   10

<210> SEQ ID NO 11

```
<211> LENGTH: 327
<212> TYPE: DNA
<213> ORGANISM: Artificial
<220> FEATURE:
<223> OTHER INFORMATION: Artificially synthesized sequence

<400> SEQUENCE: 11
caactagcag aagagaattc gtgggccctg agcgtccacg agggtgaaag tgtcacggtg      60
aattgtagtt acaagacatc cataactgcc ctacagtggt acagacagaa gtcaggcaaa     120
ggccctgccc agctaatctt aatacgttca aatgagagag agaagcgcaa tggaagactc     180
agagccaccc ttgacacctc cagccagagc agctccttgt ccatcactgc tactcggtgt     240
gaagacaccg ctgtgtactt ctgtgccgca tcttctggca gctggcaact catctttgga     300
tctggaaccc aactgacagt tatgcct                                        327

<210> SEQ ID NO 12
<211> LENGTH: 109
<212> TYPE: PRT
<213> ORGANISM: Artificial
<220> FEATURE:
<223> OTHER INFORMATION: Artificially synthesized sequence

<400> SEQUENCE: 12

Gln Leu Ala Glu Glu Asn Ser Trp Ala Leu Ser Val His Glu Gly Glu
1               5                   10                  15

Ser Val Thr Val Asn Cys Ser Tyr Lys Thr Ser Ile Thr Ala Leu Gln
            20                  25                  30

Trp Tyr Arg Gln Lys Ser Gly Lys Gly Pro Ala Gln Leu Ile Leu Ile
        35                  40                  45

Arg Ser Asn Glu Arg Glu Lys Arg Asn Gly Arg Leu Arg Ala Thr Leu
    50                  55                  60

Asp Thr Ser Ser Gln Ser Ser Ser Leu Ser Ile Thr Ala Thr Arg Cys
65                  70                  75                  80

Glu Asp Thr Ala Val Tyr Phe Cys Ala Ala Ser Ser Gly Ser Trp Gln
                85                  90                  95

Leu Ile Phe Gly Ser Gly Thr Gln Leu Thr Val Met Pro
            100                 105

<210> SEQ ID NO 13
<211> LENGTH: 5
<212> TYPE: PRT
<213> ORGANISM: Artificial
<220> FEATURE:
<223> OTHER INFORMATION: Artificially synthesized sequence

<400> SEQUENCE: 13

Thr Ser Ile Thr Ala
1               5

<210> SEQ ID NO 14
<211> LENGTH: 7
<212> TYPE: PRT
<213> ORGANISM: Artificial
<220> FEATURE:
<223> OTHER INFORMATION: Artificially synthesized sequence

<400> SEQUENCE: 14

Ile Arg Ser Asn Glu Arg Glu
1               5

<210> SEQ ID NO 15
```

```
<211> LENGTH: 10
<212> TYPE: PRT
<213> ORGANISM: Artificial
<220> FEATURE:
<223> OTHER INFORMATION: Artificially synthesized sequence

<400> SEQUENCE: 15

Ala Ala Ser Ser Gly Ser Trp Gln Leu Ile
1               5                   10

<210> SEQ ID NO 16
<211> LENGTH: 345
<212> TYPE: DNA
<213> ORGANISM: Artificial
<220> FEATURE:
<223> OTHER INFORMATION: Artificially synthesized sequence

<400> SEQUENCE: 16
aatgctggtg tcatccaaac acctaggcac aaggtgacag ggaagggaca agaagcaact        60
ctgtggtgtg agccaatttc aggacatagt gctgttttct ggtacagaca gaccattgtg       120
cagggcctgg agttcctgac ttactttcga aatcaagctc ctatagatga ttcagggatg       180
cccaaggaac gattctcagc tcagatgccc aatcagtcgc actcaactct gaagatccag       240
agcacgcaac cccaggactc agcggtgtat ctttgtgcaa gcagcttaga agggacagtg       300
gaagaaacgc tgtattttgg ctcaggaacc agactgactg ttctc                       345

<210> SEQ ID NO 17
<211> LENGTH: 115
<212> TYPE: PRT
<213> ORGANISM: Artificial
<220> FEATURE:
<223> OTHER INFORMATION: Artificially synthesized sequence

<400> SEQUENCE: 17

Asn Ala Gly Val Ile Gln Thr Pro Arg His Lys Val Thr Gly Lys Gly
1               5                   10                  15

Gln Glu Ala Thr Leu Trp Cys Glu Pro Ile Ser Gly His Ser Ala Val
                20                  25                  30

Phe Trp Tyr Arg Gln Thr Ile Val Gln Gly Leu Glu Phe Leu Thr Tyr
            35                  40                  45

Phe Arg Asn Gln Ala Pro Ile Asp Asp Ser Gly Met Pro Lys Glu Arg
        50                  55                  60

Phe Ser Ala Gln Met Pro Asn Gln Ser His Ser Thr Leu Lys Ile Gln
65                  70                  75                  80

Ser Thr Gln Pro Gln Asp Ser Ala Val Tyr Leu Cys Ala Ser Ser Leu
                85                  90                  95

Glu Gly Thr Val Glu Glu Thr Leu Tyr Phe Gly Ser Gly Thr Arg Leu
            100                 105                 110

Thr Val Leu
        115

<210> SEQ ID NO 18
<211> LENGTH: 5
<212> TYPE: PRT
<213> ORGANISM: Artificial
<220> FEATURE:
<223> OTHER INFORMATION: Artificially synthesized sequence

<400> SEQUENCE: 18

Ser Gly His Ser Ala
1               5
```

```
<210> SEQ ID NO 19
<211> LENGTH: 6
<212> TYPE: PRT
<213> ORGANISM: Artificial
<220> FEATURE:
<223> OTHER INFORMATION: Artificially synthesized sequence

<400> SEQUENCE: 19

Phe Arg Asn Gln Ala Pro
1               5

<210> SEQ ID NO 20
<211> LENGTH: 13
<212> TYPE: PRT
<213> ORGANISM: Artificial
<220> FEATURE:
<223> OTHER INFORMATION: Artificially synthesized sequence

<400> SEQUENCE: 20

Ala Ser Ser Leu Glu Gly Thr Val Glu Glu Thr Leu Tyr
1               5                   10

<210> SEQ ID NO 21
<211> LENGTH: 813
<212> TYPE: DNA
<213> ORGANISM: Artificial
<220> FEATURE:
<223> OTHER INFORMATION: Artificially synthesized sequence

<400> SEQUENCE: 21
atgaaatcct ttagtatttc cctagtggtc ctgtggcttc agctaaactg ggtgaacagc      60
caacagaagg tgcagcagag cccagaatcc ctcattgttc cagagggagg catggcctct     120
ctcaactgca cttccagtga tcgtaatgtt gactacttct ggtggtacag acagcactct     180
gggaaaagcc ccaagatgct gatgtctatc ttctccaatg gtgaaaagga agaaggcaga     240
ttcacagttc acctcaataa agccagcctg catacttccc tgcacatcag agactcccag     300
cccagtgact ctgctctcta cctctgtgca gcaagggaca gcaactatca gttgatctgg     360
ggctctggga ccaagctaat tataaagcca gatatccaga accctgaccc tgccgtgtac     420
cagctgagag actctaaatc cagtgacaag tctgtctgcc tattcaccga ttttgattct     480
caaacaaatg tgtcacaaag taaggattct gatgtgtata tcacagacaa atgcgtgcta     540
gacatgaggt ctatggactt caagagcaac agtgctgtgg cctggagcaa caaatctgac     600
tttgcatgtg caaacgcctt caacaacagc attattccag aagacacctt cttccccagc     660
ccagaaagtt cctgtgatgt caagctggtc gagaaaagct ttgaaacaga tacgaaccta     720
aactttcaaa acctgtcagt gattgggttc cgaatcctcc tcctgaaagt ggccgggttt     780
aatctgctca tgacgctgcg gctgtggtcc agc                                  813

<210> SEQ ID NO 22
<211> LENGTH: 271
<212> TYPE: PRT
<213> ORGANISM: Artificial
<220> FEATURE:
<223> OTHER INFORMATION: Artificially synthesized sequence

<400> SEQUENCE: 22

Met Lys Ser Phe Ser Ile Ser Leu Val Val Leu Trp Leu Gln Leu Asn
1               5                   10                  15

Trp Val Asn Ser Gln Gln Lys Val Gln Gln Ser Pro Glu Ser Leu Ile
```

-continued

```
              20                    25                    30

Val Pro Glu Gly Gly Met Ala Ser Leu Asn Cys Thr Ser Ser Asp Arg
        35                    40                    45

Asn Val Asp Tyr Phe Trp Trp Tyr Arg Gln His Ser Gly Lys Ser Pro
        50                    55                    60

Lys Met Leu Met Ser Ile Phe Ser Asn Gly Glu Lys Glu Glu Gly Arg
65                    70                    75                    80

Phe Thr Val His Leu Asn Lys Ala Ser Leu His Thr Ser Leu His Ile
                85                    90                    95

Arg Asp Ser Gln Pro Ser Asp Ser Ala Leu Tyr Leu Cys Ala Ala Arg
                100                   105                   110

Asp Ser Asn Tyr Gln Leu Ile Trp Gly Ser Gly Thr Lys Leu Ile Ile
        115                   120                   125

Lys Pro Asp Ile Gln Asn Pro Asp Pro Ala Val Tyr Gln Leu Arg Asp
        130                   135                   140

Ser Lys Ser Ser Asp Lys Ser Val Cys Leu Phe Thr Asp Phe Asp Ser
145                   150                   155                   160

Gln Thr Asn Val Ser Gln Ser Lys Asp Ser Asp Val Tyr Ile Thr Asp
                165                   170                   175

Lys Cys Val Leu Asp Met Arg Ser Met Asp Phe Lys Ser Asn Ser Ala
                180                   185                   190

Val Ala Trp Ser Asn Lys Ser Asp Phe Ala Cys Ala Asn Ala Phe Asn
                195                   200                   205

Asn Ser Ile Ile Pro Glu Asp Thr Phe Phe Pro Ser Pro Glu Ser Ser
        210                   215                   220

Cys Asp Val Lys Leu Val Glu Lys Ser Phe Glu Thr Asp Thr Asn Leu
225                   230                   235                   240

Asn Phe Gln Asn Leu Ser Val Ile Gly Phe Arg Ile Leu Leu Leu Lys
                245                   250                   255

Val Ala Gly Phe Asn Leu Leu Met Thr Leu Arg Leu Trp Ser Ser
                260                   265                   270
```

<210> SEQ ID NO 23
<211> LENGTH: 927
<212> TYPE: DNA
<213> ORGANISM: Artificial
<220> FEATURE:
<223> OTHER INFORMATION: Artificially synthesized sequence

<400> SEQUENCE: 23

```
atgggctcca ggctcttctt cgtgctctcc agtctcctgt gttcaaaaca catggaggct       60
gcagtcaccc aaagcccaag aaacaaggtg gcagtaacag gaggaaaggt gacattgagc      120
tgtaatcaga ctaataacca caacaacatg tactggtatc ggcaggacac ggggcatggg      180
ctgaggctga tccattattc atatggtgct ggcagcactg agaaaggaga tatccctgat      240
ggatacaagg cctccagacc aagccaagag aacttctccc tcattctgga gttggctacc      300
ccctctcaga catcagtgta cttctgtgcc agcggtgata cagggggcta tgaacagtac      360
ttcggtcccg gcaccaggct cacggtttta gaggacctga aaacgtgtt cccacccgag       420 gtcgctgtgt ttgagccatc agaagcagag atctcccaca cccaaaaggc cacactggtg      480
tgcctggcca caggcttcta ccccgaccac gtggagctga gctggtgggt gaatgggaag      540
gaggtgcaca gtggggtctg cacagacccg cagcccctca aggagcagcc cgccctcaat      600
gactccagat actgcctgag cagccgcctg agggtctcgg ccaccttctg cagaaccccc      660
```

```
cgcaaccact tccgctgtca agtccagttc tacgggctct cggagaatga cgagtggacc      720 caggatagggg ccaaacctgt cacccagatc gtcagcgccg aggcctgggg tagagcagac     780
tgtggcttca cctccgagtc ttaccagcaa ggggtcctgt ctgccaccat cctctatgag      840
atcttgctag ggaaggccac cttgtatgcc gtgctggtca gtgccctcgt gctgatggcc      900
atggtcaaga gaaaggattc cagaggc                                          927
```

<210> SEQ ID NO 24
<211> LENGTH: 309
<212> TYPE: PRT
<213> ORGANISM: Artificial
<220> FEATURE:
<223> OTHER INFORMATION: Artificially synthesized sequence

<400> SEQUENCE: 24

```
Met Gly Ser Arg Leu Phe Phe Val Leu Ser Ser Leu Leu Cys Ser Lys
1               5                   10                  15

His Met Glu Ala Ala Val Thr Gln Ser Pro Arg Asn Lys Val Ala Val
            20                  25                  30

Thr Gly Gly Lys Val Thr Leu Ser Cys Asn Gln Thr Asn Asn His Asn
        35                  40                  45

Asn Met Tyr Trp Tyr Arg Gln Asp Thr Gly His Gly Leu Arg Leu Ile
    50                  55                  60

His Tyr Ser Tyr Gly Ala Gly Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95

Glu Leu Ala Thr Pro Ser Gln Thr Ser Val Tyr Phe Cys Ala Ser Gly
            100                 105                 110

Asp Thr Gly Gly Tyr Glu Gln Tyr Phe Gly Pro Gly Thr Arg Leu Thr
            115                 120                 125

Val Leu Glu Asp Leu Lys Asn Val Phe Pro Pro Glu Val Ala Val Phe
        130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Cys Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305
```

```
<210> SEQ ID NO 25
<211> LENGTH: 804
<212> TYPE: DNA
<213> ORGANISM: Artificial
<220> FEATURE:
<223> OTHER INFORMATION: Artificially synthesized sequence

<400> SEQUENCE: 25
atgcacagcc tcctgggggtt gttgttgtgg ctgcaactga caagggtgaa tagtcaacta         60
gcagaagaga attcgtgggc cctgagcgtc cacgagggtg aaagtgtcac ggtgaattgt        120
agttacaaga catccataac tgccctacag tggtacagac agaagtcagg caaaggccct        180
gcccagctaa tcttaatacg ttcaaatgag agagagaagc gcaatggaag actcagagcc        240
acccttgaca cctccagcca gagcagctcc ttgtccatca ctgctactcg gtgtgaagac        300
accgctgtgt acttctgtgc cgcatcttct ggcagctggc aactcatctt tggatctgga        360
acccaactga cagttatgcc tgatatccag aaccctgacc ctgccgtgta ccagctgaga        420
gactctaaat ccagtgacaa gtctgtctgc ctattcaccg attttgattc tcaaacaaat        480
gtgtcacaaa gtaaggattc tgatgtgtat atcacagaca aatgcgtgct agacatgagg        540
tctatggact tcaagagcaa cagtgctgtg gcctggagca caaatctga ctttgcatgt         600 gcaaacgcct tcaacaacag cattattcca gaagacacct tcttccccag cccagaaagt        660
tcctgtgatg tcaagctggt cgagaaaagc tttgaaacag atacgaacct aaactttcaa        720
aacctgtcag tgattgggtt ccgaatcctc ctcctgaaag tggccgggtt taatctgctc        780
atgacgctgc ggctgtggtc cagc                                              804

<210> SEQ ID NO 26
<211> LENGTH: 268
<212> TYPE: PRT
<213> ORGANISM: Artificial
<220> FEATURE:
<223> OTHER INFORMATION: Artificially synthesized sequence

<400> SEQUENCE: 26

Met His Ser Leu Leu Gly Leu Leu Leu Trp Leu Gln Leu Thr Arg Val
1               5                   10                  15

Asn Ser Gln Leu Ala Glu Glu Asn Ser Trp Ala Leu Ser Val His Glu
            20                  25                  30

Gly Glu Ser Val Thr Val Asn Cys Ser Tyr Lys Thr Ser Ile Thr Ala
        35                  40                  45

Leu Gln Trp Tyr Arg Gln Lys Ser Gly Lys Gly Pro Ala Gln Leu Ile
    50                  55                  60

Leu Ile Arg Ser Asn Glu Arg Glu Lys Arg Asn Gly Arg Leu Arg Ala
65                  70                  75                  80

Thr Leu Asp Thr Ser Ser Gln Ser Ser Ser Leu Ser Ile Thr Ala Thr
                85                  90                  95

Arg Cys Glu Asp Thr Ala Val Tyr Phe Cys Ala Ala Ser Ser Gly Ser
            100                 105                 110

Trp Gln Leu Ile Phe Gly Ser Gly Thr Gln Leu Thr Val Met Pro Asp
        115                 120                 125

Ile Gln Asn Pro Asp Pro Ala Val Tyr Gln Leu Arg Asp Ser Lys Ser
    130                 135                 140

Ser Asp Lys Ser Val Cys Leu Phe Thr Asp Phe Asp Ser Gln Thr Asn
145                 150                 155                 160
```

-continued

```
Val Ser Gln Ser Lys Asp Ser Asp Val Tyr Ile Thr Asp Lys Cys Val
            165                 170                 175

Leu Asp Met Arg Ser Met Asp Phe Lys Ser Asn Ser Ala Val Ala Trp
            180                 185                 190

Ser Asn Lys Ser Asp Phe Ala Cys Ala Asn Ala Phe Asn Asn Ser Ile
        195                 200                 205

Ile Pro Glu Asp Thr Phe Phe Pro Ser Pro Glu Ser Ser Cys Asp Val
    210                 215                 220

Lys Leu Val Glu Lys Ser Phe Glu Thr Asp Thr Asn Leu Asn Phe Gln
225                 230                 235                 240

Asn Leu Ser Val Ile Gly Phe Arg Ile Leu Leu Leu Lys Val Ala Gly
            245                 250                 255

Phe Asn Leu Leu Met Thr Leu Arg Leu Trp Ser Ser
            260                 265
```

```
<210> SEQ ID NO 27
<211> LENGTH: 939
<212> TYPE: DNA
<213> ORGANISM: Artificial
<220> FEATURE:
<223> OTHER INFORMATION: Artificially synthesized sequence

<400> SEQUENCE: 27
atggccccca ggctcctttt ctgtctggtt ctttgcttct tgagagcaga accaacaaat      60
gctggtgtca tccaaacacc taggcacaag gtgacaggga agggacaaga agcaactctg     120
tggtgtgagc caatttcagg acatagtgct gtttttctggt acagacagac cattgtgcag     180
ggcctggagt tcctgactta ctttcgaaat caagctccta tagatgattc agggatgccc     240
aaggaacgat tctcagctca gatgcccaat cagtcgcact caactctgaa gatccagagc     300
acgcaacccc aggactcagc ggtgtatctt tgtgcaagca gcttagaagg gacagtggaa     360
gaaacgctgt attttggctc aggaaccaga ctgactgttc tcgaggacct gaaaaacgtg     420
ttcccacccg aggtcgctgt gtttgagcca tcagaagcag agatctccca cacccaaaag     480
gccacactgg tgtgcctggc cacaggcttc tacccgaccc acgtggagct gagctggtgg     540
gtgaatggga aggaggtgca cagtggggtc tgcacagacc cgcagccct caaggagcag     600 cccgccctca tgactccag atactgcctg agcagccgcc tgagggtctc ggccaccttc     660
tggcagaacc ccgcaacca cttccgctgt caagtccagt tctacgggct ctcggagaat     720
gacgagtgga cccaggatag ggccaaacct gtcacccaga tcgtcagcgc cgaggcctgg     780
ggtagagcag actgtggctt cacctccgag tcttaccagc aaggggtcct gtctgccacc     840
atcctctatg agatcttgct agggaaggcc accttgtatg ccgtgctggt cagtgccctc     900
gtgctgatgg ccatggtcaa gagaaaggat tccagaggc                            939
```

```
<210> SEQ ID NO 28
<211> LENGTH: 313
<212> TYPE: PRT
<213> ORGANISM: Artificial
<220> FEATURE:
<223> OTHER INFORMATION: Artificially synthesized sequence

<400> SEQUENCE: 28

Met Ala Pro Arg Leu Leu Phe Cys Leu Val Leu Cys Phe Leu Arg Ala
1               5                   10                  15

Glu Pro Thr Asn Ala Gly Val Ile Gln Thr Pro Arg His Lys Val Thr
            20                  25                  30
```

```
Gly Lys Gly Gln Glu Ala Thr Leu Trp Cys Glu Pro Ile Ser Gly His
    35                  40                  45

Ser Ala Val Phe Trp Tyr Arg Gln Thr Ile Val Gln Gly Leu Glu Phe
    50                  55                  60

Leu Thr Tyr Phe Arg Asn Gln Ala Pro Ile Asp Asp Ser Gly Met Pro
65                  70                  75                  80

Lys Glu Arg Phe Ser Ala Gln Met Pro Asn Gln Ser His Ser Thr Leu
                85                  90                  95

Lys Ile Gln Ser Thr Gln Pro Gln Asp Ser Ala Val Tyr Leu Cys Ala
                100                 105                 110

Ser Ser Leu Glu Gly Thr Val Glu Glu Thr Leu Tyr Phe Gly Ser Gly
            115                 120                 125

Thr Arg Leu Thr Val Leu Glu Asp Leu Lys Asn Val Phe Pro Pro Glu
        130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Cys Thr
                180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
        210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
                260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
        290                 295                 300

Met Val Lys Arg Lys Asp Ser Arg Gly
305                 310
```

<210> SEQ ID NO 29
<211> LENGTH: 630
<212> TYPE: DNA
<213> ORGANISM: Artificial
<220> FEATURE:
<223> OTHER INFORMATION: Artificially synthesized sequence

<400> SEQUENCE: 29

```
catatgtggg ttaatagcca gcagaaagtt cagcagagtc cggaaagcct gatcgttccg      60
gaaggcggca tggccagcct gaattgcacc agcagcgatc gcaatgttga ttacttctgg     120
tggtaccgcc agcatagcgg caaaagcccg aaaatgctga tgagcatctt cagcaatggc     180
gaaaaagaag aaggccgctt caccgttcat ctgaataaag ccagtctgca taccagcctg     240
catatccgcg atagccagcc gagcgatagc gccctgtacc tgtgcgccgc ccgcgatagc     300
aattaccagc tgatctgggg cagcggcacc aaactgatca tcaaaccgga tatccagaat     360
ccggatccgg ccgtttacca gctgcgcgat agcaaaagca gcgataaaag cgtttgcctg     420
ttcaccgatt cgatagcca gaccaatgtt agccagagca agatagcga tgtttacatc     480
```

-continued

```
accgataaat gcgttctgga tatgcgcagc atggatttca aaagcaatag cgccgttgcc     540
tggagcaata aaagcgattt cgcctgcgcc aatgccttca ataatagcat catcccggaa     600
gataccttct tcccgtctcc ggaaagcagc                                       630
```

<210> SEQ ID NO 30
<211> LENGTH: 738
<212> TYPE: DNA
<213> ORGANISM: Artificial
<220> FEATURE:
<223> OTHER INFORMATION: Artificially synthesized sequence

<400> SEQUENCE: 30

```
atgaaacata tggaagccgc cgttacccag agcccgcgca ataaagttgc cgttaccggc      60
ggcaaagtta ccctgagctg caatcagacc aataatcata ataatatgta ctggtaccgc     120
caggataccg gccatggcct gcgcctgatc cattacagct acggcgccgg cagcaccgaa     180
aaaggcgata tcccggatgg ctacaaagcc agccgcccga gccaggaaaa tttcagcctg     240
atcctggaac tggccacccc gagccagacc agcgtttact tctgcgccag cggcgatacc     300
ggcggctacg aacagtactt cggcccgggc acccgcctga ccgttctgga agatctgaaa     360 aatgtttttcc cgccggaagt tgccgttttc gaaccgagcg aagccgaaat cagccatacc     420
cagaaagcca ccctggtttg cctggccacc ggcttctacc cggatcatgt tgaactgagc     480
tggtgggtta atggcaaaga agttcatagc ggcgtttgca ccgatccgca gccgctgaaa     540
gaacagccgg ccctgaatga tagccgctac gccctgagca gccgcctgcg cgttagcgcc     600
accttctggc aggatccgcg caatcatttc cgctgccagg ttcagttcta cggcctgagc     660
gaaaatgatg aatggaccca ggatcgcgcc aaaccggtta cccagatcgt tagcgccgaa     720 gcctgggggcc gcgccgat                                                   738
```

<210> SEQ ID NO 31
<211> LENGTH: 624
<212> TYPE: DNA
<213> ORGANISM: Artificial
<220> FEATURE:
<223> OTHER INFORMATION: Artificially synthesized sequence

<400> SEQUENCE: 31

```
atgcgcgtta atagccagct ggccgaagaa aatagctggg ccctgagcgt tcatgaaggc      60
gaaagcgtta ccgttaattg cagctacaaa accagtatca ccgccctgca gtggtaccgc     120
cagaaaagcg gcaaaggccc ggcccagctg atcctgatcc gcagcaatga cgcgaaaaaa     180
cgcaatggcc gcctgcgcgc caccctggat accagcagcc agagcagcag cctgtctatc     240
accgccaccc gctgcgaaga taccgccgtt tacttctgcg ccgccagcag cggcagctgg     300
cagctgatct tcggcagcgg cacccagctg accgttatgc cggatatcca gaatccggat     360
ccggccgttt accagctgcg cgatagcaaa agcagcgata aaagcgtttg cctgttcacc     420
gatttcgata gccagaccaa tgttagccag agcaaagata gcgatgttta catcaccgat     480
aaatgcgttc tggatatgcg cagcatggat ttcaaaagca atagcgccgt tgcctggagc     540
aataaaagcg atttcgcctg cgccaatgcc ttcaataata gcatcatccc ggaagatacc     600
ttcttcccga gcccggaaag cagc                                             624
```

<210> SEQ ID NO 32
<211> LENGTH: 747
<212> TYPE: DNA

```
<213> ORGANISM: Artificial
<220> FEATURE:
<223> OTHER INFORMATION: Artificially synthesized sequence

<400> SEQUENCE: 32
atggaaccga ccaatgccgg cgttatccag accccgcgcc ataaagttac cggcaaaggc      60
caggaagcca ccctgtggtg cgaaccgatc agcggccaca gtgccgtttt ctggtaccgc     120
cagaccatcg ttcagggcct ggaattcctg acctacttcc gcaatcaggc cccgatcgat     180
gatagcggca tgccgaaaga acgcttcagc gcccagatgc cgaatcagag ccatagcacc     240
ctgaaaatcc agagcaccca gccgcaggac agcgccgttt acctgtgcgc cagcagcctg     300
gaaggcaccg ttgaagaaac cctgtacttc ggcagcggca cccgcctgac cgttctggaa     360
gatctgaaaa atgtttttcc cgccggaagtt gccgtttcg aaccgagcga agccgaaatc      420
agccataccc agaaagccac cctggtttgc ctggccaccg cttctaccc ggatcatgtt      480 gaactgagct ggtgggttaa tggcaaagaa gttcatagcg cgtttgcac cgatccgcag      540 ccgctgaaag aacagccggc cctgaatgat agccgctacg ccctgagcag ccgcctgcgc     600
gttagcgcca ccttctggca ggatccgcgc aatcatttcc gctgccaggt tcagttctac     660
ggcctgagcg aaaatgatga atggacccag gatcgcgcca aaccggttac ccagatcgtt     720
agcgccgaag cctggggccg cgccgat                                        747

<210> SEQ ID NO 33
<211> LENGTH: 15
<212> TYPE: PRT
<213> ORGANISM: Artificial
<220> FEATURE:
<223> OTHER INFORMATION: Artificially synthesized sequence

<400> SEQUENCE: 33

Gly Leu Asn Asp Ile Phe Glu Ala Gln Lys Ile Glu Trp His Glu
1               5                   10                  15

<210> SEQ ID NO 34
<211> LENGTH: 9
<212> TYPE: PRT
<213> ORGANISM: Artificial
<220> FEATURE:
<223> OTHER INFORMATION: Artificially synthesized sequence

<400> SEQUENCE: 34

Val Val Gly Ala Gly Gly Val Gly Lys
1               5

<210> SEQ ID NO 35
<211> LENGTH: 9
<212> TYPE: PRT
<213> ORGANISM: Artificial
<220> FEATURE:
<223> OTHER INFORMATION: Artificially synthesized sequence

<400> SEQUENCE: 35

Val Val Gly Ala Val Gly Val Gly Lys
1               5

<210> SEQ ID NO 36
<211> LENGTH: 9
<212> TYPE: PRT
<213> ORGANISM: Artificial
<220> FEATURE:
<223> OTHER INFORMATION: Artificially synthesized sequence
```

<400> SEQUENCE: 36

Val Val Gly Ala Asp Gly Val Gly Lys
1               5

<210> SEQ ID NO 37
<211> LENGTH: 9
<212> TYPE: PRT
<213> ORGANISM: Artificial
<220> FEATURE:
<223> OTHER INFORMATION: Artificially synthesized sequence

<400> SEQUENCE: 37

Val Val Gly Ala Cys Gly Val Gly Lys
1               5

<210> SEQ ID NO 38
<211> LENGTH: 10
<212> TYPE: PRT
<213> ORGANISM: Artificial
<220> FEATURE:
<223> OTHER INFORMATION: Artificially synthesized sequence

<400> SEQUENCE: 38

Val Val Val Gly Ala Gly Gly Val Gly Lys
1               5                   10

<210> SEQ ID NO 39
<211> LENGTH: 10
<212> TYPE: PRT
<213> ORGANISM: Artificial
<220> FEATURE:
<223> OTHER INFORMATION: Artificially synthesized sequence

<400> SEQUENCE: 39

Val Val Val Gly Ala Val Gly Val Gly Lys
1               5                   10

<210> SEQ ID NO 40
<211> LENGTH: 10
<212> TYPE: PRT
<213> ORGANISM: Artificial
<220> FEATURE:
<223> OTHER INFORMATION: Artificially synthesized sequence

<400> SEQUENCE: 40

Val Val Val Gly Ala Asp Gly Val Gly Lys
1               5                   10

<210> SEQ ID NO 41
<211> LENGTH: 10
<212> TYPE: PRT
<213> ORGANISM: Artificial
<220> FEATURE:
<223> OTHER INFORMATION: Artificially synthesized sequence

<400> SEQUENCE: 41

Val Val Val Gly Ala Cys Gly Val Gly Lys
1               5                   10

<210> SEQ ID NO 42
<211> LENGTH: 18
<212> TYPE: PRT
<213> ORGANISM: Artificial
<220> FEATURE:
<223> OTHER INFORMATION: Artificially synthesized sequence

<400> SEQUENCE: 42

```
Glu Gly Arg Gly Ser Leu Leu Thr Cys Gly Asp Val Glu Glu Asn Pro
1               5                   10                  15

Gly Pro

<210> SEQ ID NO 43
<211> LENGTH: 274
<212> TYPE: PRT
<213> ORGANISM: Artificial
<220> FEATURE:
<223> OTHER INFORMATION: Artificially synthesized sequence

<400> SEQUENCE: 43

Met Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
            115                 120                 125

Asp Leu Arg Ser Trp Thr Ala Ala Asp Met Ala Ala Gln Ile Thr Lys
        130                 135                 140

Arg Lys Trp Glu Ala Ala His Ala Ala Glu Gln Gln Arg Ala Tyr Leu
145                 150                 155                 160

Glu Gly Arg Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
        210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp

<210> SEQ ID NO 44
<211> LENGTH: 822
<212> TYPE: DNA
<213> ORGANISM: Artificial
<220> FEATURE:
<223> OTHER INFORMATION: Artificially synthesized sequence

<400> SEQUENCE: 44
```

-continued

```
atgagccata gcatgcgcta tttttatacc agcgtgagcc gcccgggccg cggcgaaccg      60
cgctttattg cggtgggcta tgtggatgat acccagtttg tgcgctttga tagcgatgcg     120
gcgagccagc gcatggaacc gcgcgcgccg tggattgaac aggaaggccc ggaatattgg     180
gatcaggaaa cccgcaacgt gaaagcgcag agccagaccg atcgcgtgga tctgggcacc     240
ctgcgcggct attataacca gagcgaagat ggcagccata ccattcagat tatgtatggc     300
tgcgatgtgg gccgatggg ccgctttctg cgcggctatc gccaggatgc gtatgatggc     360
aaagattata ttgcgctgaa cgaagatctg cgcagctgga ccgcgcgga tatggcggcg     420 cagattacca aacgcaaatg gaagcggcg catgcggcgg aacagcagcg cgcgtatctg     480
gaaggccgct gcgtggaatg gctgcgccgc tatctggaaa acggcaaaga aaccctgcag     540
cgcaccgatc cgccgaaaac ccatatgacc catcatccga ttagcgatca tgaagcgacc     600
ctgcgctgct gggcgctggg ctttatccg gcggaaatta ccctgacctg gcagcgcgat     660
ggcgaagatc agacccagga taccgaactg gtggaaaccc gccgggcggg cgatggcacc     720
tttcagaaat gggcggcggt ggtggtgccg agcggcgaag aacagcgcta tacctgccat     780
gtgcagcatg aaggcctgcc gaaaccgctg accctgcgct gg                        822
```

<210> SEQ ID NO 45
<211> LENGTH: 274
<212> TYPE: PRT
<213> ORGANISM: Artificial
<220> FEATURE:
<223> OTHER INFORMATION: Artificially synthesized sequence
<400> SEQUENCE: 45

```
Met Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gln Glu Thr
        50                  55                  60

Arg Asn Val Lys Ala Gln Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Ile Met Tyr Gly Cys Asp Val Gly Ser Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
        130                 135                 140

Arg Lys Trp Glu Ala Ala His Glu Ala Glu Gln Leu Arg Ala Tyr Leu
145                 150                 155                 160

Asp Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
        210                 215                 220
```

-continued

```
Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
            245                 250                 255

Tyr Thr Cys His Val Gln His Glu Gly Leu Pro Lys Pro Leu Thr Leu
            260                 265                 270

Arg Trp
```

```
<210> SEQ ID NO 46
<211> LENGTH: 822
<212> TYPE: DNA
<213> ORGANISM: Artificial
<220> FEATURE:
<223> OTHER INFORMATION: Artificially synthesized sequence

<400> SEQUENCE: 46
atgagccata gcatgcgcta ttttttttacc agcgtgagcc gcccgggccg cggcgaaccg      60
cgctttattg cggtgggcta tgtggatgat acccagtttg tgcgctttga tagcgatgcg     120
gcgagccagc gcatggaacc gcgcgcgccg tggattgaac aggaaggccc ggaatattgg     180
gatcaggaaa cccgcaacgt gaaagcgcag agccagaccg atcgcgtgga tctgggcacc     240
ctgcgcggct attataacca gagcgaagcg ggcagccata ccattcagat tatgtatggc     300
tgcgatgtgg cagcgatgg  ccgctttctg cgcggctatc gccaggatgc gtatgatggc     360
aaagattata ttgcgctgaa cgaagatctg cgcagctgga ccgcggcgga tatggcggcg     420
cagattacca aacgcaaatg ggaagcggcg catgaagcgg aacagctgcg cgcgtatctg     480
gatggcacct gcgtggaatg gctgcgccgc tatctggaaa acggcaaaga aaccctgcag     540
cgcaccgatc gcccgaaaac ccatatgacc atcatccga  ttagcgatca tgaagcgacc     600
ctgcgctgct gggcgctggg cttttatccg gcggaaatta ccctgacctg gcagcgcgat     660
ggcgaagatc agacccagga taccgaactg gtggaaaccc gcccggcggg cgatggcacc     720
tttcagaaat gggcggcggt ggtggtgccg agcggcgaag aacagcgcta tacctgccat     780
gtgcagcatg aaggcctgcc gaaaccgctg accctgcgct gg                        822
```

```
<210> SEQ ID NO 47
<211> LENGTH: 100
<212> TYPE: PRT
<213> ORGANISM: Artificial
<220> FEATURE:
<223> OTHER INFORMATION: Artificially synthesized sequence

<400> SEQUENCE: 47

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
            35                  40                  45

Lys Val Glu His Ser Asp Leu Ser Phe Ser Lys Asp Trp Ser Phe Tyr
        50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met
```

-continued

```
                100

<210> SEQ ID NO 48
<211> LENGTH: 300
<212> TYPE: DNA
<213> ORGANISM: Artificial
<220> FEATURE:
<223> OTHER INFORMATION: Artificially synthesized sequence

<400> SEQUENCE: 48
atgattcagc gcaccccgaa aattcaggtg tatagccgcc atccggcgga aaacggcaaa       60
agcaactttc tgaactgcta tgtgagcggc tttcatccga gcgatattga agtggatctg      120
ctgaaaaacg gcgaacgcat tgaaaaagtg gaacatagcg atctgagctt tagcaaagat      180
tggagctttt atctgctgta ttataccgaa tttaccccga ccgaaaaaga tgaatatgcg      240
tgccgcgtga accatgtgac cctgagccag ccgaaaattg tgaaatggga tcgcgatatg      300
```

SCREENING AND ANTITUMOR USE OF KRAS MUTATION SPECIFIC T CELL RECEPTOR

SEQUENCE LISTING

The instant application contains a Sequence Listing which has been submitted electronically in ASCII format and is hereby incorporated by reference in its entirety. Said ASCII copy, created on Mar. 23, 2026, is named 0259-IM01US1-FP230090US-NFOA1-Amended_sequence_listing.txt and is 38,237 bytes in size.

FIELD OF THE INVENTION

The present disclosure belongs to the field of medicine, and in particular relates to a T cell receptor (TCR) or antigen-binding fragment thereof capable of specifically recognizing an antigenic polypeptide of a tumor KRAS gene G12V mutation and G12C mutation.

BACKGROUND OF THE INVENTION

In 2011, cancer surpassed heart disease as the leading cause of death worldwide. The WHO announced in December 2013 that the number of new cancer patients worldwide exceeded 14 million each year, which was a substantial increase compared with 12.7 million in 2008. As of 2020, the cancer causes 9.6 million deaths every year, and about US$1 trillion is invested in cancer diagnosis and treatment worldwide every year.

In the early 1980s, Allison and other researchers determined the gene structure of αβ T-cell receptor (TCR) on the surface of T cells, which recognizes antigens. In the late 1980s, Boone, Rosenberg, and Old et al found that there were some tumor-specific antigens in different tumor patients, which could be recognized by T cells and then the tumor cells were specifically killed, rekindling the hope of tumor immunotherapy. A great deal of research was devoted to the research and development of therapeutic vaccines for tumors. In 2013, immune anti-cancer therapy was rated as the top 10 scientific and technological breakthroughs of the year by Science magazine.

In recent years, with the rapid development of stem cell biology, immunology, molecular technology, and tissue engineering technology, the cellular immunotherapy, as a safe and effective therapy means, becomes more and more prominent in the treatment of tumors. At present, the research and development of new cell therapy technology becomes an important research field to solve tumor and other related diseases.

Adoptive cell therapy (ACT) is a highly personalized cancer therapy, which can achieve anti-tumor effects by rebuilding the missing or weak immune system in cancer patients. ACT therapy refers to isolation of immunocompetent cells from tumor patients, expansion and functional identification in vitro, and then reinfusion to patients, so as to achieve the purpose of directly killing tumors or the purpose of indirectly killing tumor cells via stimulating the body's immune response. A limiting factor for ACT therapy is the search for antigens that are expressed only on cancerous tissues and not on normal essential tissues.

Currently, the ACT therapy may include T cell receptor engineered cell (TCR-T) therapy and chimeric antigen receptor engineered T cell (CAR-T) therapy. Through these approaches, the ACT has been shown to be effective against a variety of cancers, such as melanoma, cervical cancer, lymphoma, leukemia, choledochal carcinoma, and neuroblastoma.

At present, CAR-T has also achieved major breakthroughs in the treatment of acute/chronic granulocytic leukemia, lymphoma and other diseases, greatly improving the survival rate and quality of life for patients. However, in the study of solid tumor treatment, the therapeutic prospect of CAR-T cells is unclear due to limited specific targets.

Unlike CAR-T cells that use antibodies to target extracellular antigens, TCR is a marker on the surface of all T cells, and binds to CD3 via a non-covalent bond to form a TCR-CD3 complex. The TCR is composed of two peptide chains (α and β), and belongs to the immunoglobulin superfamily. Antigen specificity exists in the V region (CDR1, CDR2, and CDR3), wherein the CDR3 directly determines the antigen-binding specificity of TCR. TCR is expressed on 90%-95% of T cells in peripheral blood. T cells with genetically modified TCR can specifically recognize antigen molecules on the surface of tumor cells, and then generate an immune response against tumor cells.

TCR-T cell immunotherapy is a new technology of cell therapy developed in recent years, and it is a typical "precision medicine" therapy. At present, this technology has shown positive therapeutic prospects in the treatment of myeloma, melanoma, esophageal cancer, and liver cancer. TCR-T cell immunotherapy was first applied in the treatment of HIV at the end of the 20th century. In recent years, studies find that autologous immune cells engineered based on TCRs specific for MART-1, MAGE-A4, NY-ESO-1, WT-1 and other tumor antigens have shown good development prospects in the treatment of melanoma, esophageal cancer, multiple myeloma, synovial cell sarcoma and the like.

In particular, in the report in 2015 that 20 cases of multiple myeloma clinical phase I/II were subject to immunotherapy of NY-ESO-1 specific TCR engineered cells, 80% of the cases showed positive clinical effects after receiving TCR-T therapy. At present, TCR-T cell immunotherapy technology has become a hot spot in international therapy research for tumors and infectious diseases, and some technologies and products have entered the preclinical or clinical research stage.

The protein encoded by KRAS gene (Kirsten rat sarcoma virus oncogene homolog) is a small GTPase, which belongs to the RAS superprotein family and participates in intracellular signal transmission. The KRAS protein has 188 amino acids and a molecular weight of 21.6 KD, which is a guanine nucleoside-binding protein with GTPase activity. Inside the cell, the KRAS protein transitions between an inactive state and an active state; when KRAS binds to guanosine diphosphate (GDP), it is inactive, and when it binds to guanosine triphosphate (GTP), it is activated and can activate downstream signaling pathways, including MAPK signaling pathway, PI3K signaling pathway and Ral-GEFs signaling pathway. These signaling pathways play an important role in promoting cell survival, proliferation and cytokine release.

In human cancer, the KRAS is one of the most famous oncogenes in oncology and was once considered as an "undruggable" target. KRAS gene mutation occurs in nearly 90% of pancreatic cancer, 30-40% of colon cancer, 17% of endometrial cancers, 15-20% of lung cancers including lobular lung cancers, as well as cholangiocarcinoma, cervical cancer, bladder cancer, etc. KRAS gene mutation accounts for 86% of the total number of RAS gene mutations. 97% of KRAS gene mutations are mutations on amino acid residue at position 12 or position 13. The most important ones are mutations as follows: the amino acid at position 12 is altered to aspartic acid (G12D), the amino acid at position 12 is altered to valine (G12V), the amino acid at position 12 is altered to cysteine (G12C), and the amino acid at position 13 is altered to aspartic acid (G13D).

Structural studies have shown that most of these gene mutations interfere with the ability of KRAS to hydrolyze GTP. The G12D, G12V, and G13D mutations of KRAS keep KRAS bound to GTP by destroying the activity of GAP, locking KRAS in an active state by tyrosine kinase, and continuously activating downstream signaling pathways (such as PI3K, RAF-MEK-ERK (MAPK), RAL-GEF, etc.). The activation of these downstream signaling pathways will stimulate cell proliferation, migration, and ultimately promote tumorigenesis.

In recent years, covalent inhibitors have been researched and developed for KRAS mutants, which target KRAS mutants through allosteric sites, so that the affinity between KRAS mutants and GTP is reduced to achieve the purpose of "locking" its activity. For example, Amgen's AMG510, which is a KRAS-G12C inhibitor. KRAS-G12C inhibitor, MRTX1257, of MiratiTherapeutics is still in preclinical development. There is currently no relevant therapeutic medicament for other KRAS mutations, and there is also a lack of medicament for detection and treatment of tumors via the body's immune mechanism.

SUMMARY OF THE INVENTION

In human cancers, KRAS gene mutation occurs in nearly 90% of pancreatic cancer, 30-40% of colon cancer, 17% of endometrial cancers, and 15-20% of lung cancers. 97% of KRAS gene mutations are mutations on amino acid residue at position 12 or position 13. G12D, G12V, G12C, and G13D are the most important mutations. KRAS mutations can be presented to the cell surface by MHC molecules in cells and recognized by T cells to stimulate T cell immune responses, thereby eliminating tumor cells carrying KRAS mutations.

Specifically, when a KRAS mutant polypeptide is used as antigen, the body can generate a $CD8^+$ CTL (cytotoxic T lymphocyte) response. Mutations in some amino acid residues in the KRAS polypeptide can be presented by HLA molecules and recognized by T cells.

One embodiment of the present disclosure includes screening for two TCRs that specifically target KRAS-$G12V_{8-16}$ mutation (hereinafter also referred to as G12V, G12V mutation, or G12V mutation of KRAS gene) and KRAS-$G12C_{8-16}$ (hereinafter also referred to as G12C, G12C mutation, or G12C mutation of KRAS gene) of tumor KRAS gene through specific T cell receptor (TCR) single-cell screening technology.

One embodiment of the present disclosure includes providing specific T cell receptors and antigen-binding fragments thereof targeting the epitope of the G12V or G12C mutation of KRAS gene. Another embodiment of the present disclosure includes the use of the T cell receptor and antigen-binding fragment thereof in the preparation of a medicament for treatment of tumors carrying the G12V and G12C mutations of the KRAS gene.

The present disclosure is based on the above principles. By specifically binding to a complex molecule of G12V mutant polypeptide of KRAS and HLA-A11, and/or a complex molecule of G12C mutant polypeptide of KRAS and HLA-A11, or a complex molecule of KRAS-$G12V_{8-16}$ epitope and HLA-A03, the KRAS mutant polypeptide-specific TCR or antigen-binding fragment thereof in the present disclosure stimulates T cell activation, induces T cells to secrete cytokines such as IFN-γ, and then kills tumor cells expressing KRAS mutant polypeptides (especially G12V and/or G12C mutation-positive tumor cells).

In the present disclosure, the term "KRAS mutant polypeptide-specific TCR" or "murine KRAS mutant polypeptide-specific TCR" refers to a murine TCR which targets a HLA-A11 restricted CTL epitope polypeptide (with sequence of VVGAVGVGK as set forth in SEQ ID NO: 35 and/or VVGACGVGK as set forth in SEQ ID NO:37) in the KRAS mutant polypeptide, and is referred to as 1-2C TCR or 1-2C, 3-2E TCR or 3-2E in a specific embodiments of the present disclosure.

The present application includes TCRs or derivatives that specifically bind to a complex molecule of VVGAVGVGK (SEQ ID NO: 35) and/or VVGACGVGK (SEQ ID NO: 37) polypeptides derived from mutations in the amino acid at position 12 of KRAS mutant polypeptides and HLA-A11, and also include antigen-specific TCR fragments that exhibit substantially the same function as the original TCR. "Fragment of a TCR" or "antigen-binding fragment" refers to antigen-binding fragments of a TCR and TCR analogs, which generally include at least part of the antigen-binding region or variable region of the parent TCR, for example, one or more CDRs. Fragments of a TCR retain at least some of the binding specificity of the parent TCR.

When referring to ligand/receptor, antibody/antigen or other binding pairs, "specific" binding refers to determining, in a heterogeneous population of proteins and/or other biological agents, whether there is binding reaction between the protein such as VVGAVGVGK (SEQ ID NO: 35) and/or VVGACGVGK (SEQ ID NO: 37), and the HLA-A11 complex molecule. Therefore, under the specified conditions, a specific ligand/antigen binds to a specific receptor/antibody, and does not bind to other proteins present in the sample in a significant amount.

The present disclosure also provides a pharmaceutical composition containing one or two of the KRAS mutant polypeptide-specific TCRs, or an antigen-binding fragment thereof. For the preparation of the pharmaceutical composition, various desired dosage forms can be prepared by mixing the KRAS mutant polypeptide-specific TCR or an antigen-binding fragment thereof with pharmaceutically acceptable carriers or excipients. The types of dosage forms of the pharmaceutical composition of the present disclosure include, for example, as an oral preparation, tablets, powders, pills, pulvis, granules, fine granules, soft/hard capsules, film-coated tablet, pellets, sublingual tablets, ointment, etc., as a parenteral preparation, include injections, suppositories, transdermal agents, ointments, plasters, external liquids, etc., and those skilled in the art can select appropriate dosage forms according to the route of administration and the subject.

The dosing amount of the active ingredient of the pharmaceutical composition of the present disclosure varies depending on the administration subject, target organ, symptom, administration method, etc., and can be determined according to the judgment of a doctor by taking the type of dosage form, the method of administration, the age and body weight of the patient, the symptoms of the patient, and the like into consideration.

The pharmaceutical composition of the present disclosure may also contain other agents, including but not limited to cytotoxic agents, cytostatic agents, anti-angiogenesis agents or antimetabolites, tumor-targeting agents, immunostimulators or immunomodulators or TCRs in combination with cytotoxic agents, cytostatic agents or other toxic agents.

Specifically, the present disclosure provides the following embodiments.

1. A T cell receptor (TCR) or antigen-binding fragment thereof capable of binding to a complex of KRAS-G12V$_{8-16}$ epitope and HLA-A11, or a complex of KRAS-G12C$_{8-16}$ epitope and HLA-A11, or a complex of KRAS-G12V$_{8-16}$ epitope and HLA-A03 and comprising an α-chain variable region and a β-chain variable region, wherein, The TCR or antigen-binding fragment thereof comprises the following α-chain complementary determining regions (CDRs) and β-chain complementary determining regions (CDRs):

an α-chain complementary determining region CDR1 as set forth in SEQ ID NO: 3;

an α-chain complementary determining region CDR2 as set forth in SEQ ID NO: 4;

an α-chain complementary determining region CDR3 as set forth in SEQ ID NO: 5;

a β-chain complementary determining region CDR1 as set forth in SEQ ID NO: 8;

a β-chain complementary determining region CDR2 as set forth in SEQ ID NO: 9;

a β-chain complementary determining region CDR3 as set forth in SEQ ID NO: 10;

or an α-chain complementary determining region CDR1 as set forth in SEQ ID NO: 13;

an α-chain complementary determining region CDR2 as set forth in SEQ ID NO: 14;

an α-chain complementary determining region CDR3 as set forth in SEQ ID NO: 15;

a β-chain complementary determining region CDR1 as set forth in SEQ ID NO: 18;

a β-chain complementary determining region CDR2 as set forth in SEQ ID NO: 19; and a β-chain complementary determining region CDR3 as set forth in SEQ ID NO: 20;

2. The T cell receptor (TCR) or antigen-binding fragment thereof of item 1, which comprises:

an α-chain variable region as set forth in SEQ ID NO: 2, and a β-chain variable region as set forth in SEQ ID NO: 7;

or an α-chain variable region as set forth in SEQ ID NO: 12, and a β-chain variable region as set forth in SEQ ID NO: 17.

3. The TCR or antigen-binding fragment thereof according to item 1 or 2, wherein the TCR is a murine TCR, a human-mouse chimeric TCR or a humanized TCR.

4. A polynucleotide encoding the TCR or antigen-binding fragment thereof of any one of items 1-3, which is one or more sequences selected from the group consisting of SEQ ID NO:1, SEQ ID NO:6, SEQ ID NO:11, SEQ ID NO: 16.

5. An expression vector comprising the polynucleotide of item 4, wherein the expression vector is preferably a lentivirus vector.

6. A host cell comprising the expression vector of item 5.

7. A method for preparing the TCR or antigen-binding fragment thereof of any one of items 1-3, comprising:

1) culturing the host cell of item 6;

2) recovering the TCR or antigen-binding fragment thereof of any one of items 1-3 from the host cell or the culture medium thereof.

8. A pharmaceutical composition, which comprises the TCR or antigen-binding fragment thereof according to any one of items 1-3, and a pharmaceutically acceptable carrier.

9. Use of the TCR or antigen-binding fragment thereof according to any one of items 1-3 in the preparation of a medicament for increasing the level of IFN-γ cytokine secreted by T cells, wherein the medicament is, for example, a protein medicament, an ADC medicament or a medicament comprising a combination of the TCR and an antigen.

10. Use of the TCR or antigen-binding fragment thereof according to any one of items 1-3 in the preparation of a reagent for detecting a tumor cell expressing KRAS-G12V$_{8-16}$ or KRAS-G12C$_{8-16}$ mutation, or in the preparation of a reagent for detection or diagnosis of a tumor, preferably, the TCR or antigen-binding fragment specifically binds to KRAS-G12V$_{8-16}$/HLA-A11 or KRAS-G12C$_{8-16}$/HLA-A11, or the TCR or antigen-binding fragment thereof specifically binds to an HLA molecule having an antigen-binding property similar to that of HLA-A11 or HLA-A03, or specifically binds to the KRAS-G12V$_{8-16}$ or KRAS-G12C$_{8-16}$ mutant polypeptide, wherein the HLA molecule is preferably HLA-A31, HLA-A33, HLA-A68, HLA-A30.

11. Use of the TCR or antigen-binding fragment thereof according to any one of items 1-3 in the preparation of an antitumor medicament for treating a tumor patient with a G12V and G12C mutation of the KRAS gene, wherein the tumor is such as pancreas cancer, colorectal cancer, and lung cancer, such as non-small cell lung cancer; preferably, the G12V and G12C mutation of the KRAS gene are KRAS-G12V$_{8-16}$ mutation or KRAS-G12C$_{8-16}$ of the KRAS gene.

Advantages of the Invention

By using the KRAS gene G12V or G12C mutation-specific TCR of the present disclosure, T lymphocytes expressing the TCR (TCR-T) can be prepared to effectively recognize and kill KRAS gene G12V or G12C mutation-positive tumor cells, and it is expected to further inhibit the growth of tumors, especially solid tumors, and achieve the effect of tumor treatment.

The two specific T cell receptors targeting the KRAS gene G12V or G12C mutant epitope of the present disclosure and the T cells expressing said TCRs have the characteristics of high infection efficiency and high binding property, therefore, they can be used for pre-drug research and development of drugs targeting mutations associated with tumor growth and progression in experimental models, etc. Therefore, it can be used for the preparation of a medicament for the diagnosis and treatment of various tumors expressing KRAS gene mutations at various stages, especially for the preparation of a medicament for the treatment of solid tumors with high mutation frequencies.

Figure 3:
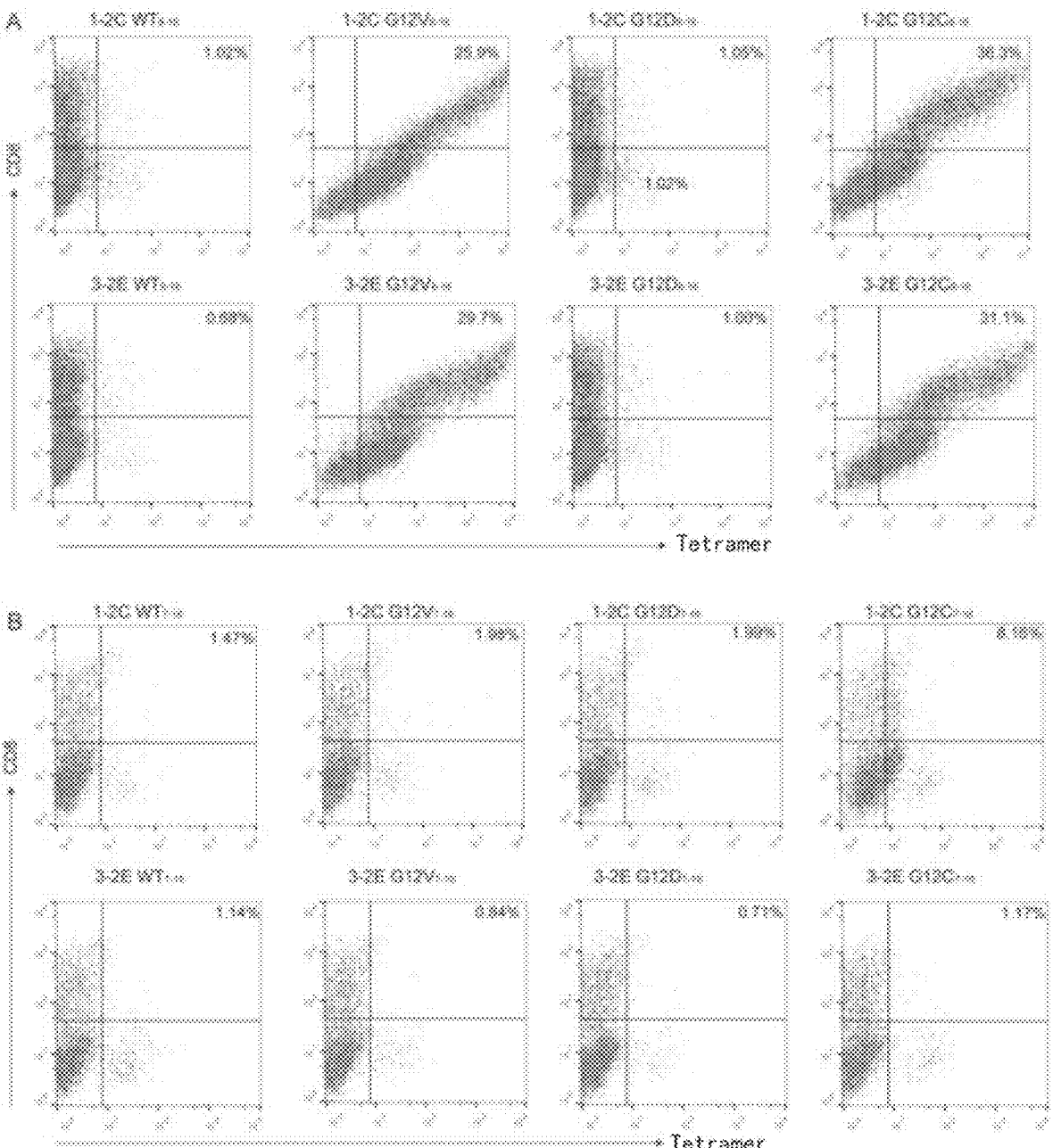

FIG. 3. Validation of 3-2E and 1-2C TCR specific binding to KRAS-G12V$_{8-16}$/HLA-A11. A represents the flow cytometry results of the specific binding to KRAS-G12V$_{8-16}$/ HLA-A11 tetramer after transient transfection of 3-2E or 1-2C TCR into 293T cells. B represents the flow cytometry results of the specific binding to KRAS-G12V$_{7-16}$/HLA-A11 tetramer after transient transfection of 1-2C or 3-2E TCR into 293T cells.

Figure 4:
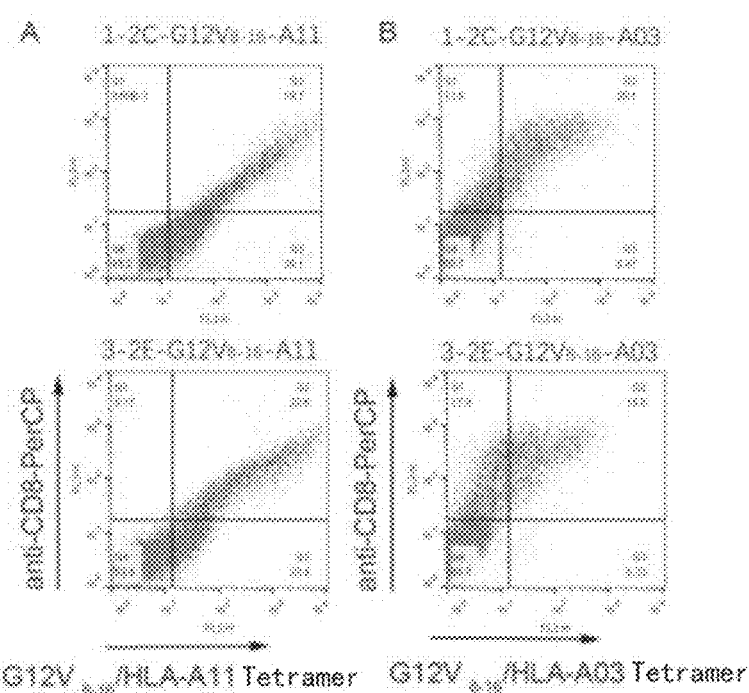

FIG. 4. Cross-recognition of 1-2C and 3-2E TCRs with KRAS-G12V$_{8-16}$/HLA-A3. Panel A represents the flow cytometry results of staining analysis of KRAS-G12V$_{8-16}$/ HLA-A11 and tetramers of 293T cells expressing 1-2C or 3-2E TCR. Panel B represents the flow cytometry results of staining analysis of KRAS-G12V$_{8-16}$/HLA-A03 and tetramers of 293T cells expressing 1-2C or 3-2E TCR.

Figure 5:
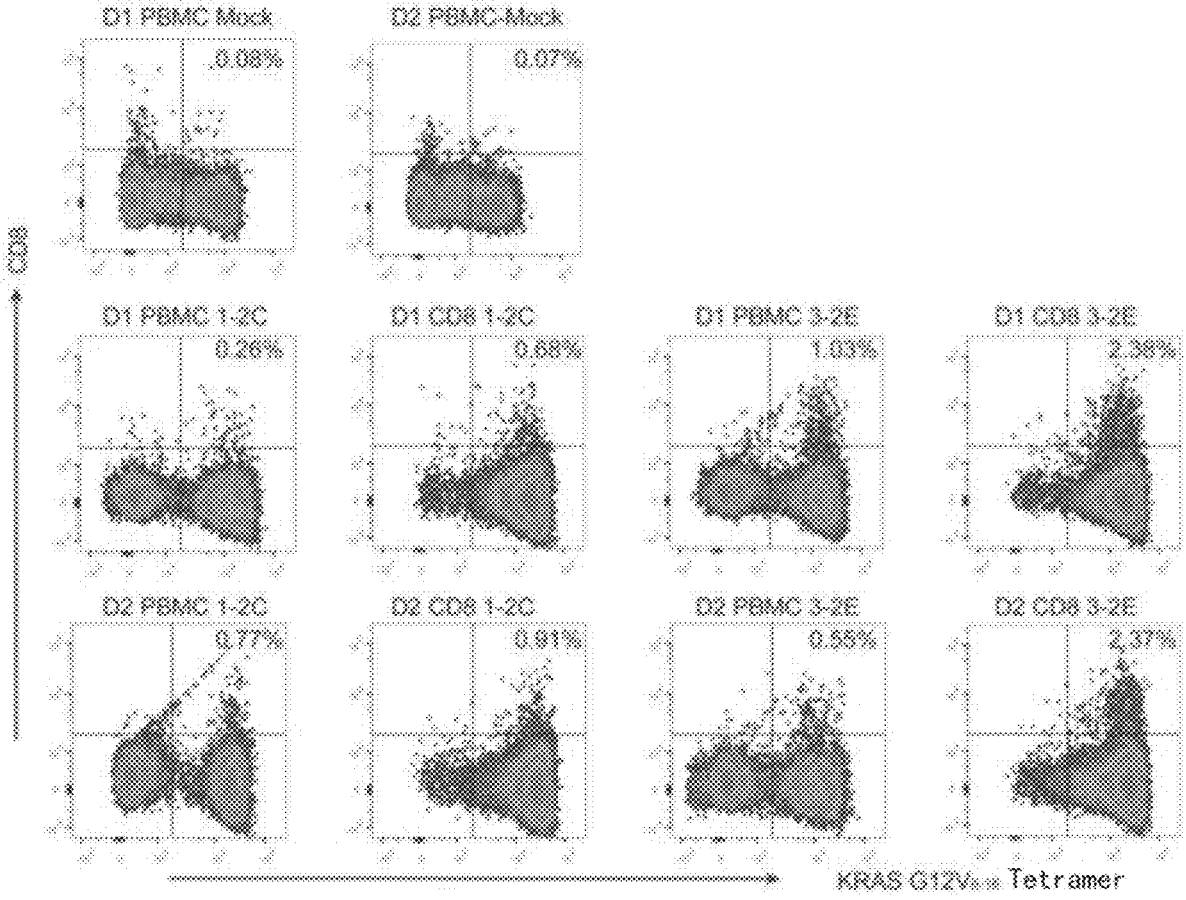

FIG. 5. Detection of infection efficiency of 1-2C or 3-2E TCR-T cells. The first row (horizontal) represents the detection of tetramers from PBMCs of two volunteers (D1 and D2) not infected with TCR lentivirus, as a negative control; the second row (horizontal) and the third row (horizontal) respectively represent TCR-T cells prepared from PBMC or CD8 T cells of volunteers, D1 (second row (horizontal) or D2 (third row (horizontal), wherein the flow cytometry staining is performed by using KRAS-G12V$_{8-16}$/HLA-A11 tetramer, and the values in the quadrants show the expression positive rate of TCR.

Figure 6:
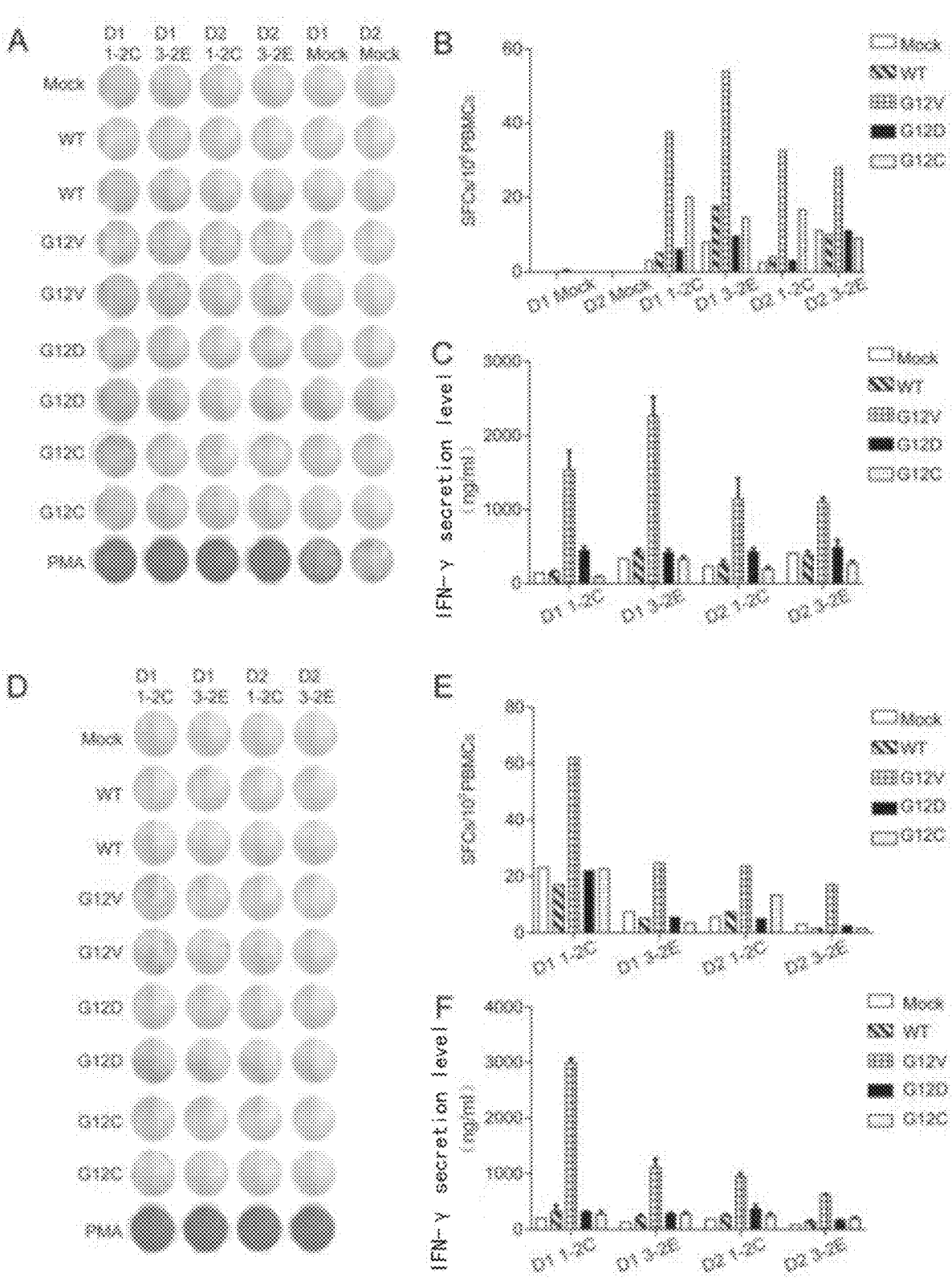

FIG. 6. Response of 1-2C or 3-2E TCR-T cells to different mutant polypeptides of KRAS. Figures A and B represent the ELISPOT images and histograms of response of 1-2C or 3-2E TCR-T cells prepared by PBMC cells to KRAS-G12 wild-type and different mutant polypeptides, wherein D1 or D2 represent the numbering of volunteers; Figure C represents the ELISA chart of IFN-γ levels produced by 1-2C or 3-2E TCR-T cells incubated with KRAS-G12 wild-type and different mutant polypeptides; the TCR-T cells incubated with medium is a negative control (mock); PMA stimulation is a positive control. Figures D, E, and F represent the ELISPOT images of 1-2C or 3-2E TCR-T cells to KRAS-G12 wild-type and different mutant polypeptides, the histogram of the results in panel D, and ELISA profile of IFN-γ levels in these cells.

Figure 7:
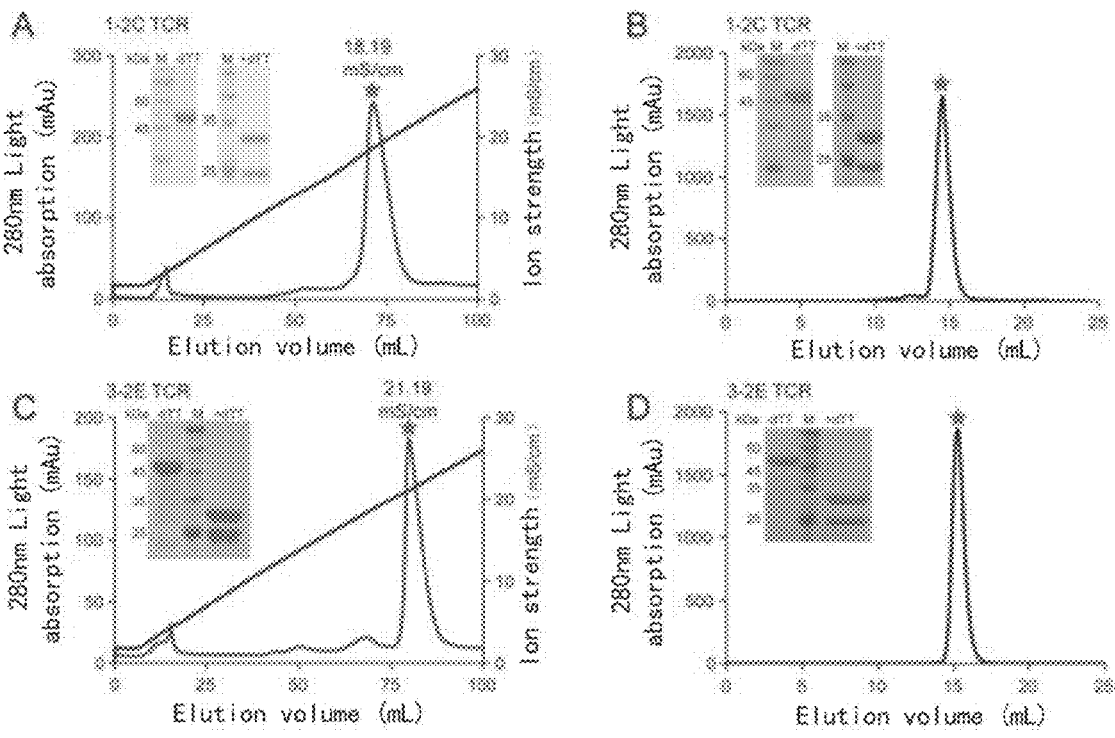

FIG. 7. In vitro renaturation and purification results of two TCR proteins, 1-2C and 3-2E. Panels A and B respectively represent the purification results of 1-2C TCR molecules after ion column and molecular sieve chromatography. Panels C and D represent the purification results of 3-2E TCR molecules after ion column and molecular sieve chromatography, respectively. The small panel represents the SDS-PAGE result of the peak protein marked with an asterisk.

Figure 8:
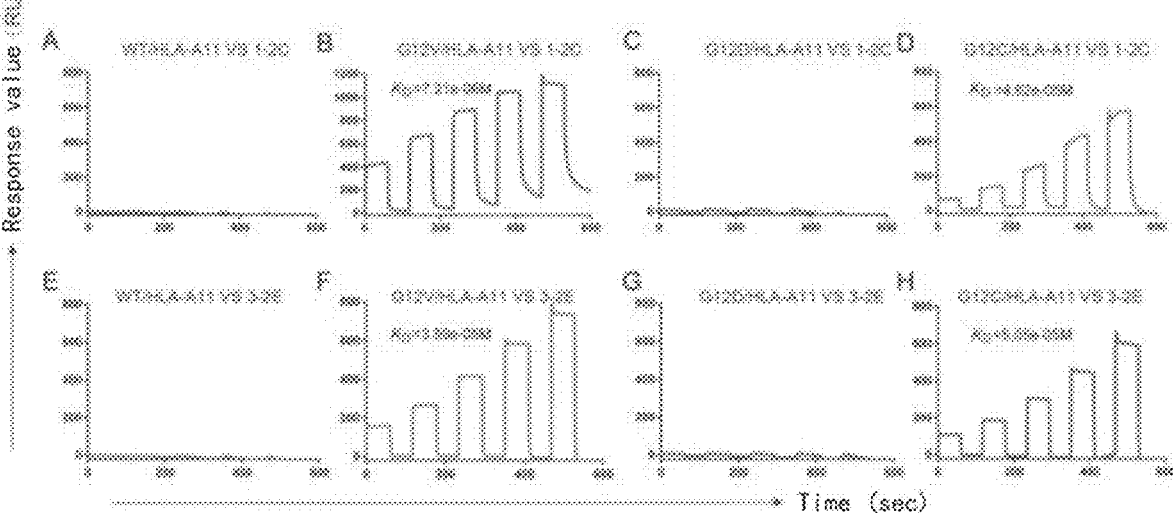

FIG. 8. The binding properties of 1-2C or 3-2E TCR to complex proteins of KRAS-G12 different mutant polypeptides and HLA-A11. Panels A-D shows the avidity detection of 1-2C TCR to the complex protein of KRAS-G12 wild-type and different mutant polypeptides with HLA-A11; Panels E-H show the avidity detection of 3-2E TCR to the complex protein of KRAS-G12 wild-type and different mutant polypeptides with HLA-A11.

Figure 9:
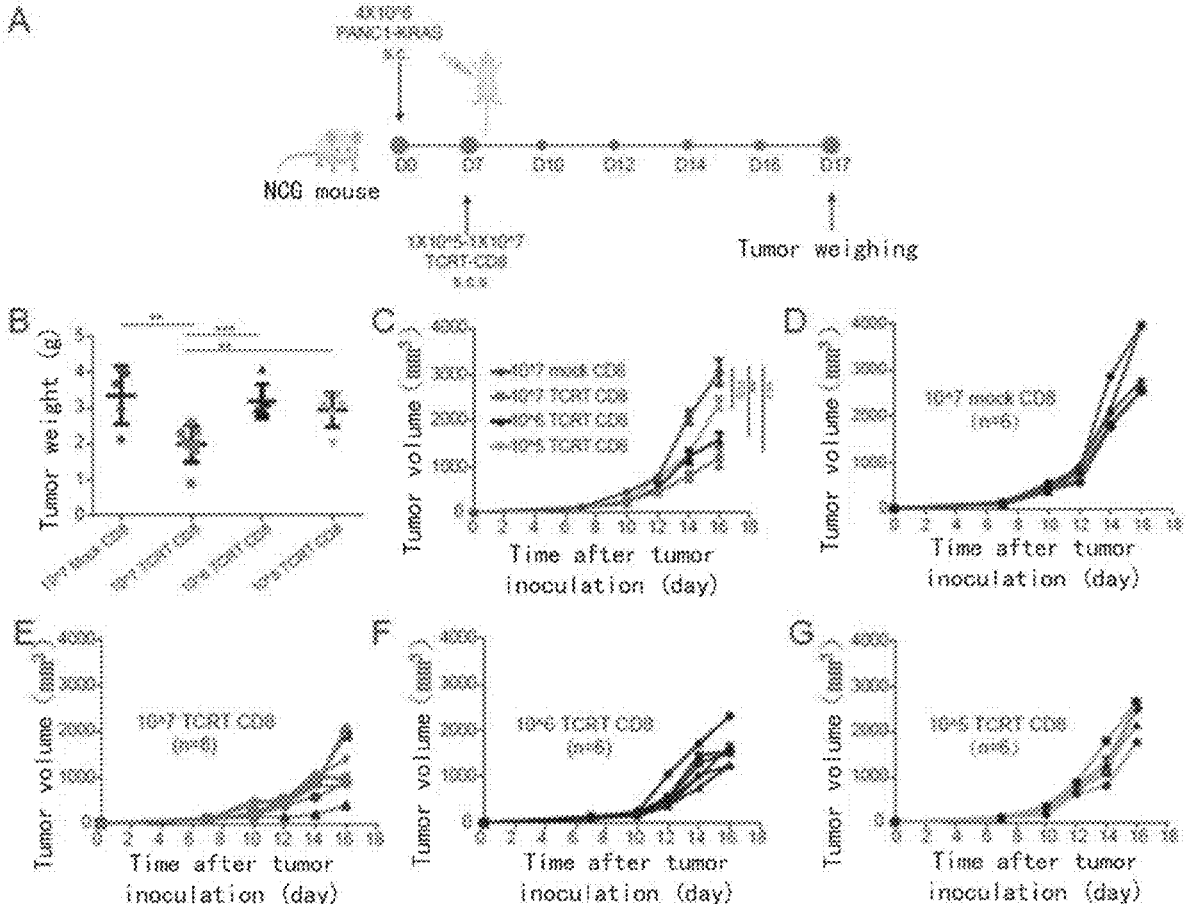

FIG. 9. Evaluation of tumor inhibition effect of 1-2C TCR-T cells in a NCG immunodeficiency mouse tumor model. Panel A represents the flow chart of the mouse tumor inhibition experiment. PANC-1 tumor cells were inoculated on day 0 (DO), TCR-T cells were injected intratumorally on day 7, and measurements were observed every 3-4 days thereafter. Panel B represents the comparison of isolated tumor weights among different treatment groups at the end of the experiment. Panel C represents the comparison of tumor volume in different treatment groups, wherein each point represents the mean±standard deviation of tumor volume in each group of mice at that time point. Panels D-G represent the tumor volume of a single mouse in each group. Statistical differences between groups were calculated by T-test, where : p<0.01, *: p<0.001; ns, p>0.05.

DETAILED DESCRIPTION OF THE INVENTION

The present disclosure further illustrates the technical solution of the present disclosure through specific embodiments and drawings, but those skilled in the art can understand that the following specific embodiments and examples are intended to illustrate the present disclosure, and should not be construed as limiting the present application in any way. It is known to those skilled in the art that many modifications can be made to the present disclosure without departing from the spirit of the present disclosure, and such modifications also fall within the scope of the present disclosure.

Unless otherwise specified, the following experimental methods are conventional experimental methods in this field. Unless otherwise specified, the experimental materials used are commercially available.

Example 1. Sorting of KRAS-G12 Mutant Polypeptide-Specific T Cell and Cloning of TCR Gene In this example, HLA-A11-restricted epitope polypeptides predicted to have KRAS-G12 mutations were first synthesized, and these polypeptides were used to immunize mice, and screening for T cell response was performed by ELISPOT experiments, and immunogenic mutant polypeptides were selected. Furthermore, tetramers of these KRAS mutant polypeptides and HLA-A11 were prepared. By staining with CD3 and CD8 antibodies together, CD3$^+$CD8$^+$ T cells were selected from splenocytes of the immunized mice and then sorted, thereby obtaining KRAS-G12 mutant polypeptide-specific T cells.

1. Prediction of HLA-Restricted Epitopes of KRAS-G12 Mutant Polypeptides

Through a NetMHC-4.0 online prediction system, the HLA-A11 restricted T cell epitope polypeptide was predicted for the polypeptide with KRAS-G12 mutation. It was found that the KRAS-G12V epitope has a strong affinity with HLA-A11.

The following polypeptides were synthesized by Sclight Biotechnology LLC: KRAS-G12 wild-type polypeptide 8-16 (VVGAGGVGK, as set forth in SEQ ID NO: 34), G12V$_{8-16}$ (VVGAVGVGK, as set forth in SEQ ID NO: 35), G12D$_{8-16}$ (VVGADGVGK, as set forth in SEQ ID NO:36), G12C$_{8-16}$ (VVGACGVGK, as set forth in SEQ ID NO:37) mutant polypeptide, KRAS-G12 wild-type polypeptide 7-16 (VVVGAGGVGK, as set forth in SEQ ID NO:38), G12V$_{7-16}$ (VVVGAVGVGK, as set forth in SEQ ID NO: 39), G12D$_{7-16}$ (VVVGADGVGK, as set forth in SEQ ID NO: 40), G12C$_{7-16}$ (VVVGACGVGK, as set forth in SEQ ID NO: 41).

2. Preparation of KRAS-G12V/HLA-A11 Tetramer

The binding properties of these polypeptides to HLA-A11, specific T cell responses, and specific TCR were evaluated and screened.

Prokaryotic codon optimization was performed on $\beta_2$m ($\beta$2-microglobulin, HLA-A11 light chain gene) (Uniprot: P61769) and HLA-A11 heavy chain gene (IMGT/HLA Acc No: HLA00043) according to conventional methods. As a result, the nucleic acid sequence of $\beta$2m was set forth in SEQ ID NO: 48, and the amino acid sequence encoded was set forth in SEQ ID NO: 47; the nucleic acid sequence of HLA-A11 heavy chain gene was set forth in SEQ ID NO: 44, and the amino acid sequence encoded was set forth in SEQ ID NO: 43. For the HLA-A11 heavy chain gene, a sequence expressing a biotin-specific binding polypeptide (Biotin-tag, the amino acid sequence as set forth in SEQ ID NO:33) was added to the C-terminus of the heavy chain gene as set forth in SEQ ID NO: 44.

These DNA sequences were synthesized by Nanjing Gen-Script, and restriction sites Nde I and Xho I were introduced therein respectively, wherein the Nde I restriction site was located at the 5' end of the sequence, and the restriction site Xho I was located at the 3' end of the sequence. By using the restriction sites Nde I and Xho I, DNA sequences of the synthesized $\beta_2$m and HLA-A11 heavy chain genes were cloned into an expression vector pET-21a (Invitrogen), respectively, to establish prokaryotic recombinant expression plasmids $\beta$2m-pET 21a and HLA-A11-pET 21a for $\beta_2$m and HLA-A11 heavy chain protein.

The two expression plasmids were transformed into E. coli. BL21(DE3) competent cells (purchased from TIANDZ Biotech) by heat stimulation, and added with IPTG to induce expression; the E. coli was broken and homogenized to extract inclusion bodies to obtain inclusion body proteins of $\beta$2m and HLA-A11 heavy chain in a state of inclusion body.

1 ml of $\beta_2$m inclusion body (30 mg/ml dissolved in 6 M Gua-HCl, 50 mM Tris pH8.0, 100 mM NaCl, 10 mM EDTA and 10 mM DTT) was added slowly to 1 L renaturing solution (20 mM Tris-HCL, 400 mM L-arginine, EDTA 2 mM, GSH/GSSG 5 mM/1 mM) containing 5 mg KRAS-G12 wild-type polypeptide 8-16, G12V8-16, G12D8-16, G12C8-16 mutant polypeptide, KRAS-G12 wild-type polypeptide 7-16, G12V7-16, G12D7-16, G12C7-16 polypeptide prepared above (synthesized by Sclight Biotechnology LLC); 1 hour later, the HLA-A11 heavy chain inclusion bodies were slowly added dropwise to the above renaturing solution at a molar ratio of $\beta$2m:HLA-A11 heavy chain=1:1, renaturing for more than 8 hours.

The renatured sample was passed through a 10 kDa filter membrane for concentration by using an ultrafiltration cup; the solution was changed to a buffer solution of 20 mM Tris-Cl, 50 mM NaCl, pH8.0 via the concentration; the solution was changed twice: 1) the sample was added to 200 ml buffer solution containing 20 mM Tris-Cl, 50 mM NaCl, pH8.0 after concentrated to about 20 ml; 2) then the sample was concentrated to about 20 ml, and added to the buffer of 20 mM Tris-Cl, 50 mM NaCl, pH8.0 again, to a volume of 100 ml, and then finally concentrated to a volume of about 10-20 ml. The sample was taken out, centrifuged at 12000 rpm for 10 min at 4° C., and the supernatant was transferred to an ultrafiltration tube and concentrated to about 0.5-1 ml, passed through a superdex200 molecular sieve (purchased from GE Healthcare) for the purification of KRAS-G12 wild-type or mutant polypeptide/HLA-A11 complex. The KRAS-G12 wild-type or mutant polypeptide//HLA-A11 complex protein peaks were collected according to the light absorption value at 280 nm (the peak value was about 15.8 mL).

The KRAS-G12 wild-type or mutant polypeptide//HLA-A11 complex protein sample purified by molecular sieve was collected in an ultrafiltration concentrator tube, concentrated to about 500 μL, and then centrifuged at 4° C. to remove the precipitate to obtain KRAS-G12 wild-type type or mutant polypeptide/HLA-A11 complex protein samples.

(2) Biotinylation Reaction

The KRAS-G12V/HLA-A11 complex protein samples obtained in step (1) were used to prepare the following biotinylation reaction system (500 μl).

Biotinylation reaction system (purchased from A VID-ITY): 500 μl in total

KRAS-G12 wild-type and mutant polypeptide/HLA-A11 complex protein samples 1 mg/ml 200 μl, Buffer A (N-bis(hydroxyethyl)glycine buffer) 50 μl, Buffer B (ATP, biotin) 50 μl, 200 μM biotin, Bir-A enzyme (3 mg/ml) 20 μl, Added with 20 mM Tris-Cl, 50 mM NaCl, pH 8.0 to a volume of 500 μl.

The above solutions were mixed well, placed on ice, and incubated overnight in a 4° C. freezer.

The above biotinylation reaction system samples were passed through Superdex200 molecular sieves for the purification of biotinylated complex to remove excess biotin. The same operations were performed as above to obtain biotinylated KRAS-G12 mutant polypeptide/HLA-A11 complex proteins of about 0.1-0.2 mg, and the peak value of KRAS-G12 wild-type or mutant polypeptide//HLA-A11 complex protein peak was about 15.8 mL (shown in FIG. 1).

Detection of Biotinylation Efficiency:

The biotinylated KRAS-G12/HLA-A11 complexes were concentrated to about 500 μl, detected by a SDS-PAGE shift test to verify the biotinylation effect.

One Sample and Two Controls were Set Up:

A. Biotinylated KRAS-G12/HLA-A11 complex sample 8 μl+molecular sieve buffer 2 μl;

B. Biotinylated KRAS-G12/HLA-A11 complex sample 8 μl+streptavidin 2 μl (20 mg/ml);

C. Streptavidin 2 μl+molecular sieve buffer 8 μl.

Figure 1:
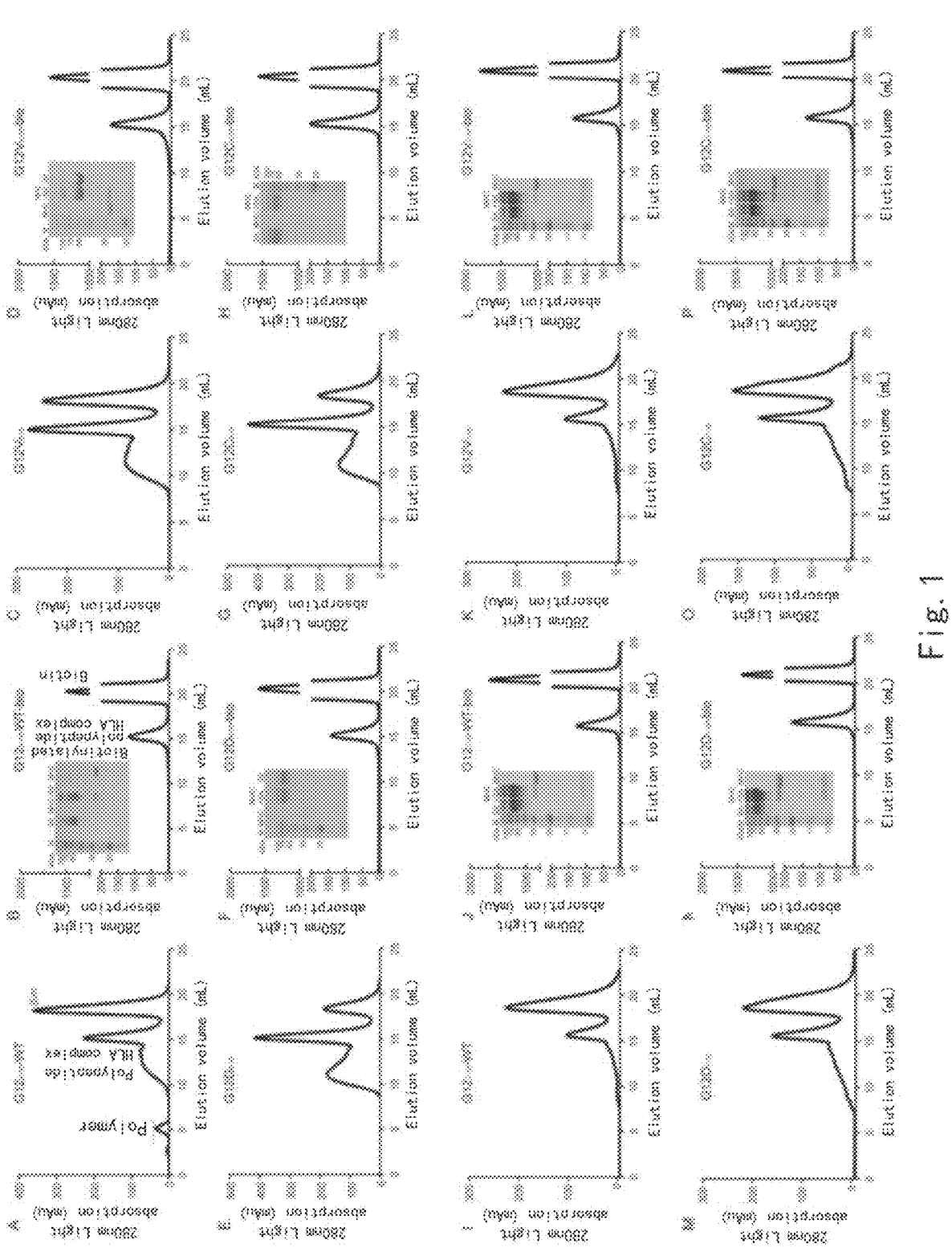
FIG. 1. Molecular sieve chromatography and biotinylation level detection results for complex proteins of different mutant polypeptides of KRAS and HLA-A11.

The above three samples were incubated on ice for 30 min and then identified by SDS-PAGE, the results were shown in FIG. 1.

The results showed that the biotinylated KRAS-G12/HLA-A11 complex could combine with streptavidin to form a macromolecule, and thus the band thereof in SDS-PAGE lagged behind. By comparing the ratio of gray scale of the SDS-PAGE band before and after biotinylation for each group of polypeptides (the gray scale of band after adding streptavidin to the KRAS-G12/HLA-A11 complex/the gray scale of band for KRAS-G12/HLA-A11 complex original protein), it could be determined that these KRAS-G12 wild-type or mutant polypeptides can be efficiently biotinylated (as shown in FIG. 1).

(3) Preparation of KRAS-G12 Wild Type and Mutant Polypeptide/HLA-A11-PE Tetramer The biotinylated KRAS-G12 wild-type and mutant peptide/HLA-A11 complex molecules were concentrated by ultrafiltration, and the biotinylated KRAS-G12 wild-type or mutant polypeptide/HLA-A11 complex molecules were added to streptavidin-PE at a molar ratio of streptavidin-PE: KRAS-G12 wild-type and mutant peptide/HLA-A11 complex=1:5 for tetramerization, and then incubated overnight at 4° C. to obtain KRAS-G12 wild-type 8-16 polypeptide, G12V$_{8-16}$, G12D$_{8-16}$, G12C$_{8-16}$ mutant polypeptide, KRAS-G12 wild-type 7-16 polypeptide, G12V$_{7-16}$, G12D$_{7-16}$, G12C$_{7-16}$/HLA-A11-PE tetramer for use.

3. Immunization of HLA-A11 Transgenic Mice with KRAS-G12V Polypeptide

In this step, HLA-A11 transgenic mice (produced by Beijing Biocytogen) were immunized by the KRAS-G12V$_{8-}$ <sub>16</sub> mutant polypeptide to induce the production of specific T cells against the KRAS-G12V$_{8-16}$ mutant polypeptide in mice in order to further obtain the specific TCR for the KRAS-G12V$_{8-16}$ mutant polypeptide.

Specifically, 100 μg of chemically synthesized KRAS-G12V$_{8-16}$ mutant polypeptide (Sclight Biotechnology LLC) was dissolved in 100 μL PBS, mixed with an equal volume of Freund's complete adjuvant and emulsified. The mixture of emulsified polypeptide and Freund's complete adjuvant was injected subcutaneously at multiple points on the back to immunize HLA-A11 transgenic mice.

One week after the first immunization, 100 μg of KRAS-G12V$_{8-16}$ mutant polypeptide was dissolved in 100 μL of PBS by the same method, mixed with an equal volume of Freund's incomplete adjuvant and emulsified, and injected in the same way to perform boost immunization. The mice were sacrificed one week later, spleens were removed, and mouse splenocytes were obtained by grinding.

4. Sorting of KRAS-G12V$_{8-16}$/HLA-A11-PE Tetramer-Specific T Cells and Amplification and Sequencing of Single-Cell TCR Genes After washed and resuspended with PBS, about $1 \times 10^7$ mouse splenocytes obtained by immunization with KRAS-G12V$_{8-16}$ mutant polypeptide in step 1 were centrifuged at 200-250 g for 10 min; washed three times with PBS containing 0.5% BSA, and then centrifuged at 200-250 g for 10 min; the mouse splenocytes were incubated with KRAS-G12V$_{8-16}$/HLA-A11-PE tetramer (obtained from the preparation of tetramer in step (3)), PerCP-Cy5-CD8 (purchased from BD) and FITC-CD3 fluorescence Antibody (purchased from BD) at a molar ratio of 1:1:1 at 25° C. for 20 minutes; the cells were washed three times with PBS containing 0.5% BSA, and centrifuged at 200-250 g for 10 minutes, and resuspend in PBS containing 0.5% BSA.

Figure 2:
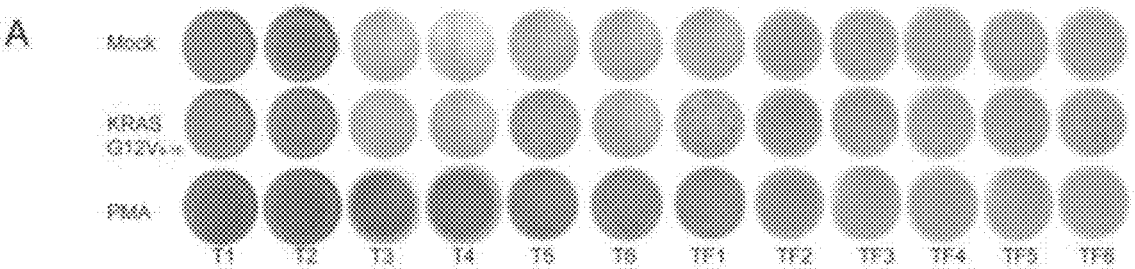
FIG. 2. Single-cell sorting of KRAS-G12V/HLA-A11 tetramer-specific T cells. Panel A represents the ELISPOT detection chart of specific T cells in spleen cells of mice immunized with KRAS-G12V polypeptide; wherein, mock represents a negative control without stimulation; KRAS-G12V$_{8-16}$ represents the polypeptide stimulation detection well; Phorbol 12-myristate 13-acetate (PMA) represents a positive control; T1-T6, TF1-TF6 represent the numbering of mouse. Panel B represents the sorting of epitope-specific T cells in splenocytes of mice immunized with polypeptides; wherein, WT represents a negative control of unimmunized mice; the abscissa represents KRAS-G12V$_{8-16}$/HLA-A11 tetramer staining, and the ordinate represents CD8 positive staining, and KRAS-G12V$_{8-16}$/HLA-A11 tetramer positive cells are the part circled in the figure.
Figure 2:
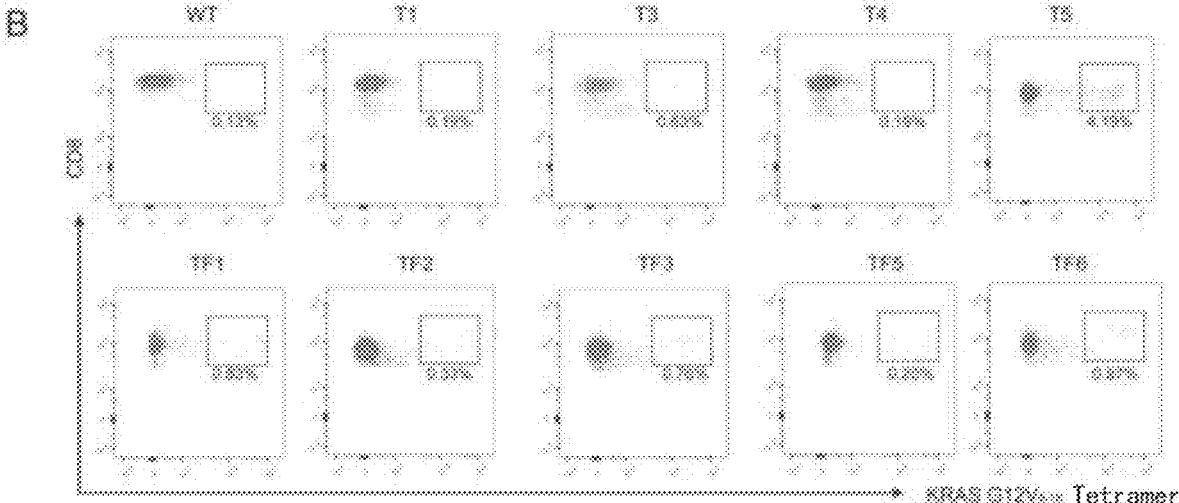

The above cells were then subjected to single cell sorting by flow cytometry. Lymphocyte subsets CD3$^+$CD8$^+$ T cells were selected, and sorted to obtained KRAS-G12V$_{8-16}$/HLA-A11-PE tetramer-positive CD8$^+$ T cells (shown in FIG. 2, wherein the tetramer-positive cells and the proportions thereof were shown in the box).

A single positive cell was sorted into a 96-well plate containing cell lysate (purchased from Tiangen Bio) and RNase inhibitor (purchased from CW Bio). Afterwards, total RNA was extracted from the KRAS-G12V$_{8-16}$/HLA-A11-PE tetramer-positive T cells in each well, and subjected to 5' RACE TCR gene amplification as follows.

5' RACE was performed by three steps: reverse transcription (RT-PCR), the first round of PCR amplification and the second round of PCR amplification. D315-FullRACE Kit from Takara was used below according to the instructions.

(1) RT-PCR: The downstream primer used was TCR gene constant region-specific primer GSP1 (purchased from Takara), and the upstream primer was a target-switch primer with oligoguanine deoxyribonucleic acid (Oligo dG) at the 3' end (Takara).

(2) The first round of PCR: the TCR cDNA obtained in the above (1) was used as a template, wherein the upstream primer was an outer linker primer 1 (5'RACE outer Primer, Takara), and the downstream primer was a specific primer for a segment of TCR constant region upstream of the constant region GSP1 (purchased from Takara), obtaining the first-round PCR product of TCR α-chain or TCR β-chain.

(3) The second round of PCR: the first-round PCR product of TCR α-chain or TCR β-chain obtained in step (2) was used as a template, wherein the upstream primer was an inner linker primer 2 (5'RACE inner Primer, Takara), and the downstream primer was a specific primer for a segment of TCR constant region upstream of the constant region GSP2 (purchased from Takara D315-FullRACE Kit), obtaining the second-round PCR products of TCR α-chain or TCR β-chain respectively.

After amplification, the second-round PCR products containing TCR α-chain and β-chain variable region genes were subjected to agarose gel electrophoresis, and the genes of interest for TCR α-chain or β-chain variable region were obtained at 500 bp. The band of interest was recovered, and the gene fragment of interest was ligated to a T vector (pMD18T, Takara) by T4 ligase. Afterwards, the ligation product was transformed into DH5α cells (purchased from Tiangen Biotechnology), and subjected to monoclonal gene sequencing (entrusted to Ruiboxingke).

After the above steps, the obtained KRAS-G12V$_{8-16}$-specific T cells were subjected to single-cell TCR gene amplification sequencing. After analysis of results, combinations of α-chain and β-chain with a high frequency were selected as new TCRs, named 1-2C TCR and 3-2E TCR, and further verified for the binding and functional effect.

Wherein, the 1-2C TCR had an α-chain variable region as set forth in SEQ ID NO: 2, and a β-chain variable region as set forth in SEQ ID NO: 7. The 3-2E TCR had an α-chain variable region as set forth in SEQ ID NO: 12, and a β-chain variable region as set forth in SEQ ID NO: 17.

Example 2. Binding Test of KRAS-G12V$_{8-16}$/HLA-A11 Tetramer to Cells Expressing 1-2C and 3-2E TCR In this Example, the inventors further confirmed that the screened 1-2C and 3-2E TCRs specially recognized KRAS-G12V$_{8-16}$/HLA-A11. In addition, the present Example also found that 1-2C and 3-2E could not only bind to KRAS-G12V$_{8-16}$ presented by HLA-A11, but also bind to KRAS-G12V$_{8-16}$ presented by HLA-A03.

1. Verification of 1-2C and 3-2E TCR Binding Specificity

Firstly, the α-chain and β-chain variable region (V region) of 1-2C and 3-2E TCR (wherein, the nucleic acid sequence of α-chain of 1-2C was set forth in SEQ ID NO: 1, and the nucleic acid sequence of β-chain of 1-2C was set forth in SEQ ID NO: 6; the nucleic acid sequence of α-chain of 3-2E was set forth in SEQ ID NO: 11, and the nucleic acid sequence of β-chain of 3-2E was set forth in SEQ ID NO: 16) genes and human TCR α-chain and β-chain constant region (C region) genes (synthesized by Hongxun Biotechnology Co., Ltd.) were linked to obtain 1-2C and 3-2E chimeric TCR α and β-chain sequences. The specific sequences of the chimeric sequences were shown in Table 1 below.

TABLE 1

| 1-2C and 3-2E chimeric TCR α and β-chain sequences | | | |
|---|---|---|---|
| | | Numbering of nucleic acid sequence | Numbering of amino acid sequence |
| 1-2C | α-chain | SEQ ID NO: 21 | SEQ ID NO: 22 |
| | β-chain | SEQ ID NO: 23 | SEQ ID NO: 24 |
| 3-2E | α-chain | SEQ ID NO: 25 | SEQ ID NO: 26 |
| | β-chain | SEQ ID NO: 27 | SEQ ID NO: 28 |

The α-chain and β-chain of 1-2C and 3-2E TCRs were connected with a T2A sequence (wherein, the amino acid sequence of T2A sequence was set forth in SEQ ID NO:42);

by using a lentivirus expression plasmid pCDH (purchased from Invitrogen) as a starting plasmid, the chimeric 1-2C and 3-2E TCR lentivirus expression vectors were constructed respectively, that is, lentivirus expression vector 1-2C-pCDH and lentivirus expression vector 3-2E-pCDH.

HEK-293T cells (purchased from ATCC) were co-transfected with the 1-2C or 3-2E-pCDH lentivirus expression vector and a CD3-CD8-pCDH plasmid expressing CD3 and CD8 (purchased from Nanjing GenScript) at a ratio of 1:1. After 24 hours of co-transfection, cells were centrifuged at 200-250 g for 10 min; washed three times with PBS containing 0.5% BSA, and centrifuged at 200-250 g for 10 min to obtain HEK-293T cells expressing 1-2C or 3-2E TCR.

Afterwards, in order to further verify the binding of 1-2C or 3-2E TCR to KRAS-G12 wild-type polypeptide and other mutant polypeptides, a staining analysis was performed on the KRAS-G12 wild-type polypeptide 8-16, $G12V_{8-16}$, $G12D_{8-16}$, $G12C_{8-16}$ mutant peptide/HLA-A11 tetramers prepared as above and the 293T cells expressing 1-2C or 3-2E TCR to evaluate the binding specificity thereof.

Specifically, the co-transfected HEK-293T cells and the KRAS-$G12V_{8-16}$/HLA-A11-PE tetramer prepared above as well as PerCP-Cy5-CD8 and FITC-CD3 antibodies (BD) were incubated at a molar ratio of 1:1:1 for 30 min; washed three times with PBS containing 0.5% BSA, centrifuged at 200-250 g for 10 min; the cells were resuspended in PBS containing 0.5% BSA for the detection of the frequency of KRAS-$G12V_{8-16}$/HLA-A11 positive T cells. Analysis was performed by using flow cytometry (shown in FIG. 3A).

Rows 1 and 2 (horizontal) in FIG. 3A represented the flow cytometry for staining analysis of co-transfected HEK-293T cells by KRAS-$G12V_{8-16}$/HLA-A11-PE tetramer. The results showed that in 293T cells transfected with 1-2C or 3-2E TCR, the cells that could bind KRAS-$G12V_{8-16}$/HLA-A11-PE tetramer accounted for about 25.9% of CD8 positive cells.

By the detection of the binding specificity of KRAS-G12 wild-type polypeptide and other mutant polypeptides/HLA-A11 tetramer, it was confirmed that 293T cells expressing 1-2C or 3-2E TCRs were unable to bind to the tetramers formed by the KRAS-G12 wild-type polypeptide or G12D8-16 and the HLA-A11, but were able to bind to the tetramers formed by the $G12C_{8-16}$ and the HLA-A11 (FIG. 3A).

The binding experiments at the cellular level showed that in addition to specifically binding to $G12V_{8-16}$/HLA-A11, 1-2C or 3-2E TCR could also specifically bind to the $G12C_{8-16}$/HLA-A11 complex.

2. Detection of Binding Specificity of 1-2C and 3-2E TCRs to KRAS-G12 10-Peptide Considering that the CD8 T cell epitope polypeptide was generally 9-10 amino acids in length and in view of the fact that the polypeptides detected above were all 9 amino acids in length (9-peptide), it could not exclude the possibility whether the 1-2C and 3-2E TCRs could bind to a 10-amino acid polypeptide (10-peptide).

According to the motif of the HLA-A11-binding polypeptide, it was found that it may still be a T cell epitope after moving the N-terminal forward by one amino acid, that is, KRAS-G12 wild-type polypeptide 7-16 (as set forth in SEQ ID NO: 38), $G12V_{7-16}$ (as set forth in SEQ ID NO: 39), $G12D_{7-16}$ (as set forth in SEQ ID NO:40), $G12C_{7-16}$ (as set forth in SEQ ID NO:41). In the present Example, by using the same conditions and operations as in Example 1, these polypeptides with a length of 10 amino acids were further prepared into tetramers, and subjected to cell binding experiments with 293T cells expressing 1-2C or 3-2E TCR, wherein the operation and conditions were the same as those for $G12D_{8-16}$ polypeptide, and the results of flow cytometry were shown in FIG. 3B.

The results showed that, according to the upper right quadrant of the flow chart, the tetramers prepared from the KRAS wild-type and mutant peptides of 10-peptide could not bind to 293T cells expressing 1-2C or 3-2E TCR. Therefore, it was further proved that the 1-2C or 3-2E TCR of the present disclosure could recognize the polypeptide epitopes of KRAS-$G12V_{8-16}$ and KRAS-$G12C_{8-16}$ with high specificity.

3. Detection of Cross Recognition Between 1-2C and 3-2E TCRs and KRAS-$G12V_{8-16}$ Presented by HLA-A03

It was known that the HLA-A11 belonged to the member of HLA-A3 superfamily, and the members of the HLA-A3 superfamily also included HLA-A03, HLA-A31, HLA-A33 and HLA-A68, etc., and the molecules in the HLA-A3 superfamily had similar antigen presentation characteristics. The antigen presentation characteristics of HLA-A3 superfamily molecules lied in that the C-terminus of the presented polypeptide was generally lysine (K) or arginine (R), and the two amino acids at the starting N-terminus of the polypeptide and the amino acid at the C-terminus were inserted into the polypeptide binding groove of the HLA molecule, and the amino acids in the middle of the polypeptide were exposed and recognized by TCR. Secondly, the α1 and α2 helices of HLA-A3 superfamily molecules such as HLA-A03, HLA-A31, HLA-A33 and HLA-A68 that could interact with TCR were more than 70% conserved.

Therefore, the TCR screened in Example 1 could also have the ability to recognize complexes formed by HLA-A3 superfamily molecules such as HLA-A03, HLA-A31, HLA-A33 and HLA-A68 and KRAS-$G12V_{8-16}$ or other mutant polypeptides. In the present Example, HLA-A03 and KRAS-$G12V_{8-16}$ were used to prepare a tetramer, and its ability of binding to the 1-2C and 3-2E TCR screened above was detected by flow cytometry, to determine its specific binding ability to KRAS-G12 mutant polypeptides presented by other HLA-A3 superfamily molecules.

Therefore, in the present example, the cross-recognition ability of 1-2C and 3-2E TCR to KRAS-$G12V_{8-16}$ presented by HLA-A03 was tested.

The sequence of HLA-A03 heavy chain gene used therein was set forth in SEQ ID NO:46, and the sequence of encoded amino acid was set forth in SEQ ID NO:45. The remaining materials and operations used were the same as those used in HLA-A11.

In the present example, a tetrameric protein of HLA-A03 (IMGT/HLA Acc No: HLA00037) and KRAS-$G12V_{8-16}$ polypeptide was also prepared by using the method shown in Example 1, and then said prepared tetrameric protein and the KRAS-$G12V_{8-16}$/HLA-A11 tetramer were used to stain and analyze 293T cells expressing 1-2C or 3-2E TCR (FIG. 4).

The results showed that the KRAS-$G12V_{8-16}$/HLA-A03 tetramer was able to significantly bind to 293T cells expressing 1-2C or 3-2E TCR (FIG. 4B, upper right quadrant).

Therefore, 1-2C or 3-2E TCR could not only bind the KRAS-$G12V_{8-16}$ polypeptide presented by HLA-A11, but also bind the KRAS-$G12V_{8-16}$ polypeptide presented by HLA-A03, indicating a wide range of application value in a wider population.

Example 3. Preparation of 1-2C and 3-2E TCR-T Cells and Response to Different Mutant Polypeptides of KRAS In the present Example, the 1-2C or 3-2E TCR gene was introduced into peripheral blood mononuclear cells (PBMC)

or CD8 T cells isolated from healthy volunteers with HLA-A11 genetic background, which were used as TCR-T effector cells. KRAS-G12 wild-type polypeptide 8-16, $G12V_{8-16}$, $G12D_{8-16}$, and $G12C_{8-16}$ mutant polypeptides were respectively added to the above TCR-T effector cell system for co-cultivation; the level of IFN-$\gamma$ secreted by effector cells after interacted with target cells presenting KRAS wild-type and mutant polypeptides was detected, and the interaction of 1-2C or 3-2E TCR and target cells expressing KRAS wild-type and mutant polypeptides/HLA-A11 was evaluated. The specific steps were as follows.

1. Preparation of Lentivirus Expressing 1-2C and 3-2E TCR

The 1-2C and 3-2E TCR lentivirus expression plasmids (1-2C-pCDH and 3-2E-pCDH) in Example 2 and the lentivirus packaging plasmids PLP1, PLP2 and VSVG (purchased from Addgene) were mixed at a ratio of PLP1:PLP2:VSVG:TCR-pCDH=20:13:5:20, and 20 μl was taken diluted in DMEM medium (1.25 ml) as a DNA solution. 20 μl polyetherimide (PEI, 1 μg/μl) was added to DMEM (1.25 ml), and all the above PEI/DMEM solution was added to the prepared DNA solution, incubated at room temperature for 15 minutes, added to 293T cells cultured in a 15 cm plate (Cell Bank, Shanghai), and mixed. After 6 hours, the culture medium was carefully aspirated and added with 25 ml of fresh culture medium for continued culturing.

After 72 hours, supernatant containing the virus was collected, which was the supernatant of the lentivirus expressing 1-2C or 3-2E TCR.

2. Preparation of 1-2C and 3-2E TCR-T Cells and Detection of TCR Expression Efficiency PBMCs were obtained by collecting the peripheral blood lymphocytes from two healthy volunteers (D1 and D2), and some of the PBMCs were negatively selected by magnetic beads (Biolegend) to isolate CD8 T cells therein. Microspheres (ThermoFisher) coated with anti-CD3/anti-CD28 were added to PBMC or CD8 T cells at a ratio of 1:1 for activation and then cultured overnight, and then 1-2C or 3-2E TCR lentivirus was added to PBMC or CD8 T cells at 1:1 volume ratio, mixed well, (wherein a well without virus infection was set as a control), and cultured in a 37° C., 5% $CO_2$ incubator. After 24 hours, the medium was replaced with complete medium and cells were continued in culture until day 10.

The anti-CD3/anti-CD28 microspheres were removed under magnetic field conditions, and washed twice with the same culture medium as that used for cell culture to obtain the 1-2C or 3-2E TCR-T effector cells of the present Example.

The above 1-2C or 3-2E TCR-T cells (cultured until day 10) prepared from PBMC or CD8 T cells were cultured, and detected by flow cytometry by staining with KRAS-$G12V_{8-16}$/HLA-A11 tetramer in the same manner as that in Example 2, and the expression of 1-2C or 3-2E TCR was confirmed (FIG. 5, upper right quadrant).

The results showed that tetramer-positive T cells with various positive rates of 0.26%-2.38% could be detected in the 1-2C, 3-2E TCR-T cells prepared by PBMC or CD8+ T cells from volunteer D1 and volunteer D2, wherein the positive rates in PBMC were 0.26% and 0.77% for 1-2C, 1.03% and 0.55% for 3-2E; the positive rates in CD8+ T cells were 0.68% and 0.91% for 1-2C, and 2.38% and 2.37% for 3-2E.

As can be seen, these TCR-T effector cells of the present disclosure could specifically bind KRAS-$G12V_{8-16}$/HLA-A11.

3. Detection of Immune Response of 1-2C and 3-2E TCR-T Cells to KRAS Wild-Type and Mutant Polypeptides The level of secreted IFN-$\gamma$ was detected after interaction of 1-2C or 3-2E TCR-T cells and target cells presenting KRAS wild-type and mutant polypeptides by using different T cell detection methods (IFN-$\gamma$-ELISPOT and IFN-$\gamma$-ELISA).

The 1-2C or 3-2E TCR-T cells prepared from the PBMCs or CD8 T cells of two volunteers (D1 and D2) and the PBMCs of two volunteers (D1 and D2) were mixed respectively at a ratio of 1:1, as antigen-presenting cells, and then they were added to a ELISPOT plate pre-coated with anti-IFN-$\gamma$ antibodies with a volume of 100 μl at 1□$10^5$ cells/well, and KRAS wild-type and mutant polypeptides (100 μl volume, 10 μg/ml) were also added; the plate was placed in a culture incubator for 18 hours at 37° C., 100% humidity, 5% $CO_2$; a sample stimulated with PMA/Ionomycin (ION) (100 μl volume, 1 μg/ml) or a sample only containing 100 μl medium was set up as positive or negative control, respectively. ELISPOT spot analysis was performed on specific T cells producing IFN-$\gamma$, and the results were shown in FIG. 6A-B, D-E.

Furthermore, the 1-2C or 3-2E TCR-T cells prepared from the PBMCs or CD8 T cells of two volunteers (D1 and D2) were mixed with the PBMCs of two volunteers (D1 and D2) at a ratio of 1:1, serving as antigen-presenting cells. The prepared cell suspension was plated into a 96-well plate, 100 μl cell suspension ($2 \times 10^5$ cells) per well, with three replicates for each well, wherein, in the PMA/Ionomycin (ION) group, 1 μl PMA/Ionomycin mixed solution was added to 250 μl cell culture medium (250×), and diluted in advance to be used as a working solution, which was used as a positive stimulation control. T cells (D1 mock and D2 mock) not infected with 1-2C or 3-2E TCR lentivirus were added in parallel as negative controls. After cultured at 37° C. for 20 h, the supernatant in the 96-well plate was taken, and centrifuged at 500 g for 5 min to remove remaining cells, and supernatant was added to a ELISA detection plate (BD) coated with anti-IFN-$\gamma$ antibodies (BD) to detect the IFN-$\gamma$ level in the supernatant, and the results were shown in FIGS. 6C and F.

The ELISPOT results showed that the 1-2C or 3-2E TCR-T cells prepared from the PBMCs of D1 and D2 volunteers could generate a strong T cell immune response to the KRAS-G12V mutant polypeptide, and also had a certain level of cross-response to the KRAS-G12C mutant polypeptide. On the other hand, T cell responses to KRAS wild-type and KRAS-G12D mutant polypeptide were not detected (FIG. 6A-B). In 1-2C or 3-2E TCR-T cells prepared by CD8 T cells from D1 and D2 volunteers, T cell immune responses similar to those in TCR-T cells prepared by PBMC could be detected (FIG. 6D-E).

The ELISA results of IFN-$\gamma$ levels showed that 1-2C or 3-2E TCR-T cells prepared by PBMC or CD8 T cells from D1 and D2 volunteers could generate a strong T cell immune response to the KRAS-G12V mutant polypeptide, and increase the IFN-$\gamma$ levels, whereas T cell responses to KRAS wild-type and KRAS-G12D mutant polypeptides were not detected (FIGS. 6C and F).

Therefore, the 1-2C and 3-2E TCR-T cells could specifically recognize the target cells presenting KRAS-$G12V_{8-16}$/HLA-A11, had a certain cross-response to target cells presenting KRAS-$G12C_{8-16}$, and could specifically secrete the cytokine IFN-$\gamma$. In view of the potential cytotoxic effect of CD8+ T cells on target cells, it was suggested that the 1-2C and 3-2E TCR-T cells of the present disclosure had a potential activity of killing target cell and a potential value for treatment of tumor.

Example 4. Analysis of the Binding Properties of
1-2C and 3-2E TCRs to KRAS Mutant Polypeptide
Epitopes In order to accurately determine the binding properties
and affinities of 1-2C and 3-2E TCRs to KRAS different
mutant polypeptides/HLA-A11 complex proteins, the affini-
ties at the protein level were further detected by surface
plasmon resonance (SPR). The functional region of 1-2C or
3-2E TCR was the extracellular region, and the extracellular
region without a transmembrane region was a soluble pro-
tein, therefore, the extracellular region of 1-2C or 3-2E TCR
was synthesized. The specific steps were as follows.
1. Expression and Purification of TCR Protein The extracellular region genes of 1-2C or 3-2E TCR
α-chain and β-chain were subjected to prokaryotic codon
optimization, and the DNA sequences of 1-2C and 3-2E
TCR chimeric α-chain and β-chain extracellular region were
synthesized respectively (1-2C: α-chain, SEQ ID NO: 29;
β-chain, SEQ ID NO: 30; 3-2E: α-chain, SEQ ID NO: 31;
β-chain, SEQ ID NO: 32), wherein, the 1-2C TCR had an
α-chain variable region as set forth in SEQ ID NO: 2, and
a β-chain variable region as set forth in SEQ ID NO: 7. The
3-2E TCR had an α-chain variable region as set forth in SEQ
ID NO: 12, and a β-chain variable region as set forth in SEQ
ID NO: 17. Restriction sites Nde I and Xho I were intro-
duced therein respectively, wherein the Nde I restriction site
was located at the 5' end of the sequence, and the restriction
site Xho I was located at the 3' end of the sequence. The
DNA sequences of extracellular regions of the synthesized
1-2C or 3-2E TCR α-chain and β-chain were cloned into an
expression vector pET21 a (Invitrogen) by using restriction
sites Nde I and Xho I, thereby constructing a prokaryotic
recombinant expression plasmid for 1-2C or 3-2E TCR
α-chain and β-chain extracellular region proteins.

The expression plasmid was transferred into *E. coli*.BL21
(DE3) competent cells by heat shock method, added with
IPTG to induce expression, and the extracellular region
proteins of 1-2C or 3-2E TCR α-chain and β-chain in a state
of inclusion body were obtained.

6 ml of the extracellular region proteins of 1-2C or 3-2E
TCR α-chain and β-chain in a state of inclusion body
(wherein, 30 mg/ml of each inclusion body was dissolved in
a solution containing 6 M Gua-HCl, 50 mM Tris pH8.0, 100
mM NaCl, 10 mM EDTA and 10 mM DTT) was dropped
into 1 L prepared renaturing solution (5 M urea, 20 mM
Tris-HCL, 400 mM L-arginine, EDTA 2 mM, GSH/GSSG 5
mM/1 mM) at a mass ratio of 2:1, and then concentrated
with a concentration cup (Millipore), wherein the dropping
of the extracellular region proteins was performed by twice,
3 mL each time, with a interval of at least 8 h.

After concentration, the solution was placed in a dialysate
of 4 L deionized water and 4 L 10 mM Tris, pH 8.0, and
dialyzed for 24 h, respectively. Afterwards, the protein of
interest was subjected to crude purification by Source 15Q
ion exchange chromatography, and identified by SDS-
PAGE.

Specifically, the protein of interest was concentrated with
a concentration cup (Millipore), with the buffer being
changed to a 20 mM Tris-HCL, 150 mM NaCL, pH 8.0
buffer, purified with Superdex200 μg molecular sieves (GE
Healthcare) to obtain about 2-3 mg of 1-2C or 3-2E TCR
protein, and the protein of interest was detected by reduced
(with dithiothreitol (DTT)) and non-reduced (without dith-
iothreitol (DTT)) SDS-PAGE (FIG. 7).

The results showed that 1-2C TCR was eluted under 18.19
mS/cm, and 3-2E TCR was eluted under 3-2E 21.19 mS/cm;

the peak of protein of interest appeared at the elution volume
of 15 mL in molecular sieve chromatography. The SDS-
PAGE showed that 1-2C or 3-2E was in a state of αβ
heterodimer, and the band size in non-reduced SDS-PAGE
without DTT was about 52 KD; whereas, in the reduced
SDS-PAGE added with DTT, disulfide bonds between the
α-chain and the β-chain were broken, showing bands around
24 KD and 28 KD respectively (FIG. 7).
2. SPR Detection and Analysis The 1-2C and 3-2E TCR proteins prepared by the same in
vitro renaturing steps as those in Example 1, and the
biotinylated KRAS wild type and different mutant 9-peptide/
HLA-A11 complex protein prepared in Example 1 were
transferred into SPR buffer (10 mM HEPES-HCl, 150 mM
Na—Cl, 0.005% Tween-20, pH 7.4). KRAS wild-type and
different mutant 9-peptide/HLA-A11 complex proteins were
diluted to 20 μg/ml and immobilized on a SA chip (GE
Health), after which serially diluted 1-2C and 3-2E TCR
proteins (0 μM, 6.25 μM, 12.5 μM, 25 μM, 50 μM, 100 μM)
were passed through each channel of the SA chip respec-
tively; BIA evaluation software was used to analyze the
binding kinetic parameters and calculate the affinity con-
stant. The affinities of 1-2C and 3-2E TCR to wild-type and
KRAS wild-type and different mutant 9-peptide/HLA-A11
complex proteins were detected (FIG. 8).

FIG. 8 showed that the binding of 1-2C TCR to KRAS-
G12V$_{8-16}$/HLA-A11 presented a fast binding and fast dis-
sociation mode, with a binding affinity (KD) of 7.21 μM,
whereas the binding affinity (KD) to KRAS-G12C$_{8-16}$/HLA-
A11 was 46.2 μM, which was significantly lower than that
to KRAS-G12V$_{8-16}$ epitope.

1-2C could not bind KRAS wild-type KRAS-G128-16/
HLA-A11 and KRAS-G12D$_{8-16}$/HLA-A11. The binding
affinity (KD) of 3-2E TCR to KRAS-G12V$_{8-16}$/HLA-A11
was 35.9 μM, significantly lower than that of 1-2C; the
binding affinity (KD) to KRAS-G12C$_{8-16}$/HLA-A11 was
50.5 μM, which was at the same level as that to KRAS-
G12V$_{8-16}$.

Similar to 1-2C, 3-2E TCR could not bind KRAS wild-
type KRAS-G128-16/HLA-A11 and KRAS-G12D$_{8-16}$/
HLA-A11.

Therefore, as can be seen from the SPR results, 1-2C TCR
and 3-2E TCR could specifically bind KRAS-G12V$_{8-16}$/
HLA-A11; 1-2C TCR had a certain cross-response to
KRAS-G12C$_{8-16}$/HLA-A11, and the affinity of 1-2C TCR to
KRAS-G12C$_{8-16}$/HLA-A11 was at the same level as that to
KRAS-G12V. Therefore, 1-2C and 3-2E TCR had good
binding property and affinity, and thus it could be speculated
that when used in anti-tumor therapy, 1-2C and 3-2E TCR
could generate IFN-γ against tumor cells carrying the G12V
and G12C mutations of KRAS, and then kill tumor cells to
achieve the effect of treating tumors.

Example 5. Tumor Inhibition Activity of 1-2C
TCR-T Cells in a Tumor Mouse Model

In this Example, a PANC-1 tumor model of NCG immu-
nodeficient mice was used to evaluate the tumor inhibition
effect of 1-2C TCR-T cells.

The tumor inhibition in NCG mice by TCR-T cells
included the following steps:
1. Construction of PANC-1 Tumor Model in NCG Mice NCG mice were obtained from Nanjing University-Nan-
jing Institute of Biomedicine. Each NCG mouse was sub-
cutaneously inoculated with PANC-1 tumor cells carrying the KRAS-G12V mutation gene (Beijing Union Cell Resource Center), and a human immune system was established in NCG mice:

a) the number of PANC-1 cells inoculated: $4 \times 10^6$ cells/ 200 μL/mouse;

b) inoculation site: subcutaneously on the back;

2. 1-2C TCR-T Cell Therapy

On the 7th day after PANC-1 tumor cell inoculation in NCG mice, the tumor volume grew to about 200 mm³, and the 1-2C TCR-T cells prepared from the PBMCs of two volunteers (D1 and D2) in Example 3 were injected into PANC-1 tumor of NCG mice via multiple intratumoral injections;

a) number of 1-2C TCR-T cells inoculated: three doses, $1 \times 10^7$, $1 \times 10^6$, $1 \times 10^5$ cells/200 μL/mouse, respectively;

b) inoculation site: intratumoral;

3. Grouping and Treatment:

About 1 week after tumor cell injection, mice with uniform tumor formation were selected for grouping, and then intratumoral injection of 1-2C TCR-T cells was performed. In this Example, the group of infecting T cells ($1 \times 10^7$) not introduced with TCR was used as the negative control, with 6 mice in each group, wherein 3 mice for TCR-T cell treatment groups prepared in D1 and D2. The information and treatment of each group were shown in the table below:

TABLE 2

Grouping and treatment of mice

| Grouping of mice | Cell injection and dose | Number of mice |
|---|---|---|
| Negative control group | $1 \times 10^7$, 200 μL | 6 mice |
| treatment group by high-dose of 1-2C TCR-T cells | $1 \times 10^7$, 200 μL | 6 mice |

TABLE 2-continued

Grouping and treatment of mice

| Grouping of mice | Cell injection and dose | Number of mice |
|---|---|---|
| treatment group by medium-dose of 1-2C TCR-T cells | $1 \times 10^6$, 200 μL | 6 mice |
| treatment group by low-dose of 1-2C TCR-T cells | $1 \times 10^5$, 200 μL | 6 mice |

After tumor formation, the tumor size was detected every three to four days, and the experiment was terminated when the maximum tumor volume of the mice reached 4000 mm³, and then the mice were sacrificed and the tumors were separated and weighed.

4. Observation of Treatment Effect:

1) Tumor Size Detection:

A) the diameter of tumor was measured by a caliper, wherein the unit was mm, and the calculation formula was: $v = \frac{1}{2} \times a \times b \times b$ (a representing the long diameter, and b representing the short diameter);

b) The experiment was terminated after the last observation, and the tumor tissue was separated and directly weighed.

The results showed that, in the treatment groups injected with $1 \times 10^7$ high-dose and $1 \times 10^6$ medium-dose of 1-2C TCR-T cells, the tumor volumes were significantly smaller than that in the negative control group (T test, $p < 0.01$) (FIG. 9C), whereas there was no significant difference in tumor volume between the group injected with $1 \times 10^5$ low-dose of 1-2C TCR-T cells and the negative control group (T test, $p > 0.05$). Analysis of tumor weight in each group at the end of the experiment showed that the tumor weight in the high-dose group was significantly lower than that in the negative control group (FIG. 9A). The results of this Example show that 1-2C TCR-T cells can effectively inhibit tumor growth, and the tumor inhibition activity is significantly dose-dependent, and thus 1-2C TCR-T cells has a potential for tumor treatment (as shown in FIG. 9).

We claim:

1. A T cell receptor (TCR) or antigen-binding fragment thereof, capable of binding to a complex of KRAS-G12V$_{8-16}$ epitope of SEQ ID NO: 35 and HLA-A11, a complex of KRAS-G12C$_{8-16}$ epitope of SEQ ID NO: 37 and HLA-A11, or a complex of KRAS-G12V$_{8-16}$ epitope of SEQ ID NO: 35 and HLA-A03 and comprising an α-chain variable region and a β-chain variable region, wherein the TCR or antigen-binding fragment thereof comprises the following α-chain complementarity determining regions (CDRs) and β-chain complementarity determining regions (CDRs):

an α-chain complementarity determining region CDR1 comprising SEQ ID NO: 3;
an α-chain complementarity determining region CDR2 comprising SEQ ID NO: 4;
an α-chain complementarity determining region CDR3 comprising SEQ ID NO: 5;
a β-chain complementarity determining region CDR1 comprising SEQ ID NO: 8;
a β-chain complementarity determining region CDR2 comprising SEQ ID NO: 9; and
a β-chain complementarity determining region CDR3 comprising SEQ ID NO: 10;
or
an α-chain complementarity determining region CDR1 comprising SEQ ID NO: 13;
an α-chain complementarity determining region CDR2 comprising SEQ ID NO: 14;
an α-chain complementarity determining region CDR3 comprising SEQ ID NO: 15;
a β-chain complementarity determining region CDR1 comprising SEQ ID NO: 18;
a β-chain complementarity determining region CDR2 comprising SEQ ID NO: 19; and
a β-chain complementarity determining region CDR3 comprising SEQ ID NO: 20.

2. The T cell receptor (TCR) or antigen-binding fragment thereof of claim 1, which comprises:

an α-chain variable region comprising SEQ ID NO: 2, and
a β-chain variable region comprising SEQ ID NO: 7;
or
an α-chain variable region as set forth in SEQ ID NO: 12, and
a β-chain variable region comprising SEQ ID NO: 17.

3. The TCR or antigen-binding fragment thereof according to claim 1, wherein the TCR is a murine TCR, a human-mouse chimeric TCR or a humanized TCR.

4. A polynucleotide encoding the TCR or antigen-binding fragment thereof of claim 1, which is one or more sequences selected from the group consisting of SEQ ID NO: 1, SEQ ID NO:6, SEQ ID NO:11, and SEQ ID NO:16.

5. An expression vector comprising the polynucleotide of claim 4, wherein the expression vector is a lentivirus vector.

6. A host cell comprising the expression vector of claim 5.

7. A method for preparing the TCR or antigen-binding fragment thereof of claim 1, comprising:

i) culturing a host cell comprising an expression vector, wherein the expression vector comprises a polynucleotide, and the polynucleotide comprises one or more sequences selected from the group consisting of SEQ ID NO:1, SEQ ID NO:6, SEQ ID NO:11, and SEQ ID NO:16;

ii) recovering the TCR or antigen-binding fragment thereof of claim 1 from the host cell or a culture medium thereof.

8. A pharmaceutical composition, which comprises the TCR or antigen-binding fragment thereof according to claim 1, and a pharmaceutically acceptable carrier.

9. A method for increasing interferon (IFN)-γ cytokine level secreted by a T cell, comprising contacting a T cell expressing the TCR or antigen-binding fragment thereof of claim 1 with a polypeptide comprising a KRAS-G12V$_{8-16}$ mutation of SEQ ID NO: 35 or a KRAS-G12C$_{8-16}$ mutation of SEQ ID NO: 37, thereby increasing IFN-γ cytokine level secreted by the T cell.

10. A method for detecting a tumor cell expressing a KRAS-G12V$_{8-16}$ mutation of SEQ ID NO: 35 or a KRAS-G12C$_{8-16}$ mutation of SEQ ID NO: 37, comprising contacting a protein comprising the TCR or antigen-binding fragment thereof of claim 1 with the tumor cell to be detected, thereby detecting presence or absence of the tumor cell expressing the KRAS-G12V$_{8-16}$ mutation or the KRAS-G12C$_{8-16}$ mutation.

11. A method for treating a tumor with a KRAS-G12V$_{8-16}$ mutation of SEQ ID NO: 35 and/or a KRAS-G12C8-16 mutation of SEQ ID NO: 37 of a KRAS gene in a patient, comprising administering to the patient a T cell expressing the TCR or antigen-binding fragment thereof of claim 1, thereby treating the patient.

12. The method of claim 11, wherein the tumor is selected from pancreas cancer, colorectal cancer, or lung cancer.

13. The method of claim 12, wherein the tumor is non-small cell lung cancer.

14. The method of claim 11, wherein the TCR or antigen-binding fragment thereof comprises:

an α-chain variable region comprising SEQ ID NO: 2, and a β-chain variable region comprising SEQ ID NO: 7;

or an α-chain variable region comprising SEQ ID NO: 12, and a β-chain variable region comprising SEQ ID NO: 17.

15. The method of claim 11, wherein the TCR is a murine TCR, a human-mouse chimeric TCR or a humanized TCR.

\* \* \* \* \*